United States Patent [19]

Oh et al.

[11] Patent Number: 5,534,620

[45] Date of Patent: Jul. 9, 1996

[54] METHOD OF HETEROGENOUS PURIFICATION USING A BIDENTATE CONJUGATE

[75] Inventors: Chan S. Oh, Diamond Bar; Elizabeth K. Kearns, Chino, both of Calif.

[73] Assignee: Beckman Instruments, Inc., Fullerton, Calif.

[21] Appl. No.: 450,652

[22] Filed: May 25, 1995

Related U.S. Application Data

[63] Continuation of Ser. No. 984,171, Nov. 20, 1992, abandoned, which is a continuation-in-part of Ser. No. 536,058, Jun. 8, 1990, Pat. No. 5,196,351, which is a continuation of Ser. No. 103,237, Sep. 30, 1987, abandoned.

[51] Int. Cl.$^6$ ............................ C07K 1/22; C12N 11/00; C12N 11/06; G01N 33/547

[52] U.S. Cl. ............................ 530/413; 435/6; 435/174; 435/177; 435/181; 436/501; 436/543; 530/412; 530/344; 530/345

[58] Field of Search ................................ 530/413, 412, 530/344, 345; 436/501, 536, 543; 435/174, 177, 181, 6

[56] References Cited

U.S. PATENT DOCUMENTS

| | | | |
|---|---|---|---|
| 3,935,074 | 1/1976 | Rubenstein et al. | 195/103.5 R |
| 4,130,462 | 12/1978 | Rubenstein et al. | 195/103.5 R |
| 4,134,792 | 1/1979 | Boguslaski et al. | 195/99 |
| 4,228,237 | 10/1980 | Hevey et al. | 435/7 |
| 4,238,565 | 12/1980 | Hornby et al. | 435/7 |
| 4,243,749 | 1/1981 | Sadeh et al. | 435/7 |
| 4,264,449 | 4/1981 | Dodd | 210/656 |
| 4,298,685 | 11/1981 | Parikh et al. | 435/7 |
| 4,506,009 | 3/1985 | Lenhoff et al. | 435/7 |

(List continued on next page.)

FOREIGN PATENT DOCUMENTS

| | | |
|---|---|---|
| 0177191 | 4/1986 | European Pat. Off. . |
| 0183901 | 6/1986 | European Pat. Off. . |
| 0220899 | 5/1987 | European Pat. Off. . |
| 0315317 | 5/1989 | European Pat. Off. . |
| 2029011 | 3/1980 | United Kingdom . |
| 2084317 | 4/1982 | United Kingdom . |

OTHER PUBLICATIONS

Morris, D. L. et al., "Flavin Adenine Dinucleotide as a Label in Homogeneous Colorimetric Immunoassays", Anal. Chem (1981) vol. 53, pp. 658–665.

Ngo, T. T., et al., "Enzyme Modulators as Tools For The Development of Homogeneous Enzyme Immunoassays". FEBS Letters (1979) vol. 116 (2) pp. 285–288.

Larsson, P. O., et al., "Affinity Precipitation of Enzymes" FEBS Letters (1979), vol. 98 (2) pp. 333–338.

Oellerich, M., et al. "Enzyme–Immunoassay: A Review 1)", J. Clin. Chem. Biochem (1983) vol. 22, pp. 895–904.

Gibbons, I., et al., "Homogeneous Enzyme Immunoassay for Proteins Employing B–Galactosidase". Analytical Biochemistry (1980), vol. 102, pp. 167–17.

Flygare, S., et al., "Affinity Precipitation of Dehydrogenases". Analytical Biochemistry (1983) vol. 133, pp. 409–416.

Sternberg, J. C., et al., "A Rate Nephelometer for Measuring Specific Proteins by Immunoprecipitin Reactions". Clin. Chem. (1977), vol. 23/8 pp. 1456–1464.

(List continued on next page.)

Primary Examiner—W. Gary Jones
Assistant Examiner—Paul B. Tran
Attorney, Agent, or Firm—William H. May; Gary T. Hampson

[57] ABSTRACT

A novel heterogenous purification method is disclosed. The method removes a macromolecule from a liquid by allowing the macromolecule to undergo a specific binding affinity reaction with a bidentate conjugate. The method is carried out by immobilizing the bidentate conjugate on a solid phase, contacting the bidentate conjugate with the liquid comprising the macromolecule, and separating the immobilized bidentate conjugate from contact with the liquid, thereby removing the macromolecule from the liquid to obtain either purified macromolecule or a purified liquid.

17 Claims, 5 Drawing Sheets

U.S. PATENT DOCUMENTS

| | | | |
|---|---|---|---|
| 4,550,075 | 10/1985 | Bacquet et al. | 435/7 |
| 4,604,365 | 8/1986 | O'Neill et al. | 436/528 |
| 4,608,336 | 8/1986 | Benovic et al. | 435/7 |
| 4,687,732 | 8/1987 | Ward et al. | 435/6 |
| 4,711,955 | 12/1987 | Ward et al. | 536/29 |
| 4,722,906 | 2/1988 | Guire | 436/501 |
| 4,760,142 | 7/1988 | Primes et al. | |
| 4,791,067 | 12/1988 | Sheiman et al. | 436/513 |
| 4,791,193 | 12/1988 | Okonogi et al. | 530/416 |
| 4,879,247 | 11/1989 | Ohlson | 436/527 |
| 4,883,598 | 11/1989 | Riethorst et al. | 210/656 |
| 4,981,785 | 1/1991 | Nayak | 435/7 |
| 5,168,057 | 12/1992 | Oh et al. | 435/174 |
| 5,196,351 | 3/1993 | Harris et al. | 436/501 |
| 5,219,764 | 6/1993 | Huber et al. | 430/536 |

OTHER PUBLICATIONS

Green, N. M., et al., "The Use of Bifunctional Biotinyl Compounds to Determine the Arrangement of Subunits in Avidin", The Biochemical Journal (1971), vol. 125, pp. 781–791.

Flygare, S. et al., "Affinity Precipitation of Enzymes", Applied Biochemistry and Biotechnology (1982), vol. 7, pp. 59–61.

Woods, V., et al., "The Capacity of Bifunctional Antigens to Bridge Antibody Molecules and to Mediate Cell Cooperation", Immunochemistry (1975), vol. 12, pp. 379–382.

Alkan, S. S., et al., "Antigen Recognition and the Immune Response", The Journal of Expermental Medicine (1972) vol. 135, pp. 1228–1246.

Brigatl, D. J., et al., "Detection of Viral Genormes in Cultured Cells and Paraffin–Embedded Tissue Sections Using Biotin–Labeled Hybridization Prodes", Virology (1983), vol. 126, pp. 32–50.

"The Journal of Bilogical Chemistry", G. Redeuilh, C. Secco & E–E. Baulieu, vol. 260, No. 7, Issue of Apr. 10, pp. 3996–4002, 1985 by The American Society of Biological Chemists, Inc.

Review "The Avidin–Biotin Complex in Bioanalystical Applications", M. Wilchek and E. Bayer, Analytical Biochemistry 171, 1–32 (1988).

Chemical Abstracts, vol. 77, 1972, pp. 510–511, by Quill.

Microbiology, third edition, (1980) by B. D. Davis, et al., pp. 292–355.

Journal of Molecular Biology (1971) 56, 203–206, article by N. M. Green et al.

Journal of Experimental Medicine 136 (1972) 1478–1483, article by M. E. Bush et al.

The Biochemical Journal 125:3 (1971), 781–791, article by N. M. Green et al.

Molecular Biology and Biotechnology, J. M. Walker (1988), chapter 12: "Immobilized Biocatalysts", pp. 235–258.

Techniques in Molecular Biology, J. M. Walker (1987), chapter 3, pp. 55–97.

METHOD OF HETEROGENOUS PURIFICATION USING A BIDENTATE CONJUGATE

CROSS REFERENCE

This is a continuation of application Ser. No. 07/984,171 filed on Nov. 20, 1992, now abandoned, which is a continuation-in-part of application Ser. No. 07/536,058, filed Jun. 8, 1990, by Paul C. Harris and Chan S. Oh, entitled "Novel Bidentate Conjugate and Method of Use Thereof", now U.S. Pat. No. 5,196,351 which is a continuation of application Ser. No. 07/103,237, filed Sep. 30, 1987, entitled "Novel Bidentate Conjugate and Method of Use Thereof" by Paul C. Harris and Chan S. Oh, now abandoned. Both these applications are incorporated herein by reference.

BACKGROUND OF THE INVENTION

1. Specific Binding Assays

Methods for measuring immunochemical or other types of specific binding reactions have become widely accepted in the field of medical testing in recent years. Generally speaking, an immunochemical reaction involves the reaction between at least one antigen and at least one antibody. An antigen is ordinarily a substance, such as a protein or carbohydrate, which is capable of inducing an immune response; i.e., antibody production, when introduced into an animal or human body. The antibodies produced as a result of the immune response are bivalent in nature, generally being depicted as a "Y" wherein each arm of the "Y" is capable of binding to the antigen which induced production of the antibody. The presence of a particular antigen or antibody in a patient's test sample may indicate a disease state or a bodily condition, such as pregnancy. An immunochemical reaction is one type of specific binding reaction.

Antibody fragments are often used in addition to or in place of whole antibodies in an immunoassay. Generally, there are three different types of antibody fragments. The first type of fragment is designated as either Fab or F(ab), and is a single arm of the antibody which has been directly cleaved from the whole antibody, usually through digestion by the enzyme papain. Each Fab fragment is monovalent, and has a molecular weight of about 50,000 Daltons, compared to the approximate 150,000 Dalton size of the whole antibody. The second type of fragment is designated as F(ab')$_2$, and consists of both antibody arms, still linked together, but minus the tail which is removed by pepsin digestion. The divalent F(ab')$_2$ fragment has a molecular weight of about 100,000 Daltons, and can be further cleaved into two separate monovalent Fab' fragments (the third type of antibody fragment), also designated as F(ab'), each having a molecular weight of about 50,000 Daltons.

The site on the antigen to which an arm of the antibody binds is referred to as an epitope. Most antigens are polyepitopic, having multiple, and often repeating, binding sites for antibodies. It is the polyepitopic nature of antigens and the bivalent character of antibodies, including F(ab')$_2$ fragments, which enable large antibody:antigen complexes of varying sizes, otherwise known as immunocomplexes, to be formed in an immunoassay.

One particular type of immunoassay which takes advantage of this feature is the sandwich immunoassay, wherein a ternary immunocomplex is formed. The most common type of sandwich immunoassay employs a first insolubilized antibody, usually bound to a solid support, and a second labeled antibody. Each antibody is specific for the antigen of interest (i.e., the analyte to be measured) and binds to a different epitope on the antigen. Preferably, the first antibody binds to an epitope which is remote from the epitope to which the second antibody binds. A ternary complex of insoluble antibody:antigen:labeled antibody is formed where the antigen of interest is contacted with the first and second antibodies. Because each antibody is required to bind to only one antigen, all three types of antibody fragments may be used in this type of method. The presence or absence of the antigen of interest is indicated by the presence or absence of the labeled antibody on the solid support. Ordinarily, the insolubilized phase of the reaction must be separated from the liquid phase in order for either the bound or free labeled antibody to be quantified. Such a reaction is referred to as a heterogenous type of reaction, due to the required separation step.

Nephelometry and turbidimetry require the formation of large aggregates of, e.g., antibody and antigen. Because each antibody must bind to two different antigen molecules, the monovalent Fab and Fab' fragments are generally ineffective in these methods. The large aggregates cause a change in the light scatter of the solution, and are capable of measurement by nephelometric or turbidimetric methods. These methods do not require the use of traditional labels, such as enzymes, radioactive isotopes, or fluorescent or chemiluminescent compounds, to detect the amount of complex formed. Rather, nephelometric and turbidimetric methods directly measure the amount of complexation. Because no separation step is required, nephelometry and turbidimetry are referred to as homogenous immunoassays.

The multiepitopic nature of the antigen and bivalent character of the antibody will, depending on the amount of antigen and/or antibody present, allow the formation of antigen:antibody complexes large enough to scatter light. Ordinarily, an excess of antibody is used in conjunction with a finite amount of antigen obtained from, e.g., a patient's blood, serum, cerebrospinal fluid (CSF), or urine sample. In such a case, the amount of antigen present in the sample will be the limiting factor in determining the amount and size of antigen:antibody aggregates formed.

In turbidimetry, the reduction of light transmitted through the suspension of particles, or aggregates, is measured. The reduction is caused by reflection, scatter, and absorption of the light by the aggregates. In nephelometry, it is the light scattered or reflected toward a detector that is not in the direct path of light which is measured. In both turbidimetry and nephelometry, the rate of change in light scatter may also be measured as an indication of the amount of antigen present.

Nephelometric procedures have become a convenient method for monitoring antigen:antibody reactions at an early stage, by detecting the rate of growth of complexes capable of scattering light before the complexes separate out of solution as immunoprecipitates. The growth of these complexes begins as a build-up of aggregates which ultimately become large enough to function as "scattering centers". Sternberg, J. C., A Rate Nephelometer for Measuring Specific Proteins by Immunoprecipitation Reactions, *Clin. Chem.*, 23:8, 1456–1464 (1977). The formation of scattering centers can be accelerated by the use of hydrophilic nonionic polymers, such as dextran or polyethylene glycol, which increase the probability of protein-protein interaction by excluding a significant fraction of water. The use of polymers in an immunonephelometric assay also gives the advantages of increased sensitivity and less antiserum consumption.

2. Nephelometric Inhibition Immunoassays for Haptens

Haptens pose a unique problem in immunoassay methods. Haptens are relatively small monovalent molecules, sometimes regarded as incomplete or fragmentary antigens. One common class of haptens is drugs. Theophylline, for example, is a member of this particular subclass of haptens. A hapten is, in and of itself, incapable of inducing an immune response in a human or animal body. This is because haptens are generally too small to be recognized by the body's immune system. However, when coupled to a carrier, such as a protein, the hapten:carrier protein conjugate acts as an antigen which is large enough to induce antibody production. In this way, antibodies can be raised against a hapten. Unlike the relatively large antigens, however, the small hapten molecule is not itself multiepitopic. For this reason, haptens are incapable of forming large complexes or agglomerates with the antibody which has been produced against the hapten.

Consequently, in order to perform nephelometric or turbidimetric assays for haptens, such as in therapeutic drug monitoring, a technique known as nephelometric inhibition immunoassay (NIIA) has been developed, wherein the hapten acts as an inhibitor to complex formation. In traditional NIIA, a second conjugate known as a "developer antigen" is used to develop complexes of sufficient size to cause detectable light scattering. The developer antigen is formed from a second carrier, also usually a protein, conjugated to a multiplicity of hapten molecules. In this way the developer antigen acts as a "polyvalent hapten" which is capable of aggregating with more than one antibody molecule to ultimately form scattering centers. The second carrier protein is sometimes referred to as the "label". The monovalent free hapten present in a patient's test sample acts to inhibit the amount of developer antigen:antibody complexing, by binding to one or both arms of the antibody molecule, thereby reducing complex formation and diminishing the amount of light scatter. Because of the nature of the inhibition immunoassay, both the amount and the rate of the increase detected in light scatter are inversely proportional to the amount of hapten present in the patient's sample.

Several problems have been encountered with prior art turbidimetric or nephelometric inhibition immunoassays. One problem concerns the developer antigen reagent. The traditional developer antigen is generally unstable and requires special storage conditions. The requirement for special storage conditions arises from the fact that the carrier protein of the developer antigen, being a natural proteinaceous substance, degrades during manufacture as well as during storage. At room temperature, a typical developer antigen can be expected to last only about eight hours. Even at refrigeration temperatures, most developer antigens exhibit a shelf life of only about six months. This greatly compounds the problems of manufacture and distribution and adds to the cost of such products. Moreover, because the carrier protein for the developer antigen is derived from natural sources, considerable variation is encountered in the properties of these proteins. The traditional developer antigen reagent must be carefully prepared, purified, and characterized to insure uniform reactivity. This characterization process is the most expensive aspect of the manufacture of prior art developer antigens.

Prior art NIIA's have also been found to possess limited sensitivity in relation to other types of immunoassays, such as the sandwich immunoassay. This sensitivity limitation results primarily from the scatter caused by other components of the serum sample. For this reason, a test sample must be diluted significantly before being added to the reaction medium of an NIIA, thereby also diluting the concentration of analyte in the reaction medium. In other types of immunoassays, such as the sandwich immunoassay, about 100–200)L of sample are typically added to the reaction medium. In contrast, only about 1–3 µL of sample are ordinarily injected into the reaction medium for a NIIA. One method that has been suggested for improving sensitivity involves optimizing the hapten:carrier ratio of the developer antigen, as disclosed in U.S. Pat. No. 4,604,365. High and low hapten:carrier ratios have been reported to result in moderate sensitivity, with improved sensitivity being observed at intermediate ratios. This method, however, is time consuming and fails to show marked increases in NIIA sensitivity.

Yet another problem encountered with the prior art NIIA's involves a phenomenon known as "nonproductive binding". Nonproductive binding occurs, for example, where the two binding arms of the same antibody bind to two hapten moieties on the same developer antigen. In such an instance, there can be no cross-linking with other developer antigens, because there is no free arm on the antibody to bind with another developer antigen. This results in the inefficient use of expensive antibody and developer antigen reagents.

Due to the ease and convenience of the homogenous turbidimetric and nephelometric inhibition immunoassays for haptens, it would be advantageous to have a stable developer antigen which can readily be manufactured to possess consistent characteristics and which exhibits a long shelf life at room temperatures. It would also be advantageous to improve the sensitivity of the NIIA and to reduce the occurrence of nonproductive binding.

3. Prior Art Bifunctional Conjugates

There are several small molecule bifunctional conjugates which exist in the prior art. What is meant by the term "small molecule bifunctional conjugate" is a conjugate which employs two small molecules which are linked together through a spacer moiety. The spacer moiety may be so small as to comprise only one chemical bond (i.e., zero atoms in the spacer). Generally, these molecules are on the order of about 7,000 Daltons or smaller in size. Both molecules act as small molecule ligands and, as such, are each capable of interacting with a substance having a specific binding affinity for the small molecule; i.e., its specific binding partner. This definition specifically excludes conjugates which employ one or more large molecules and/or conjugates which employ one or more chemical moieties which do not have a specific binding partner. For example, the typical enzyme labeled antibody in a sandwich immunoassay is excluded for both reasons; i.e., the antibody moiety is a large macromolecule, on the order of about 150,000 Daltons in size, and the enzyme moiety, although it acts on a substrate, is not generally considered to be the specific binding partner for the substrate. Also excluded are heterobifunctional cross-linking agents which utilize two chemically reactive groups rather than two small molecule ligands, one at each end of the conjugate.

There are two classes of small molecule bifunctional conjugates existing in the prior art. The first class of conjugates, known as the homobifunctional conjugate employs identical chemical moieties at each end of the conjugate. The homobifunctional conjugates are generally designed to bring together, or unite, the identical specific binding partner with which each chemical moiety interacts. Where the specific binding partner is polyvalent, large aggregates may be formed.

For example, a Bis-NAD homobifunctional conjugate has been proposed as a precipitating agent for enzymes. Larsson, P. and Mosbach, K., Affinity Precipitation of Enzymes, *Elsevier/North-Holland Biomedical Press*, 98:2, 333–330 (1979). The Bis-NAD conjugate, comprising two NAD moieties separated by a 17 Å spacer moiety, is capable of precipitating the enzyme lactate dehydrogenase (LDH) out of solution by specifically binding to a large LDH molecule at each end of the Bis-NAD. Because each large LDH molecule has multiple binding sites for NAD, large aggregates, similar to those formed in nephelometry, can be obtained. These large aggregates precipitate out of solution carrying along the enzyme. Similar uses of Bis-nucleotides of varying spacer lengths have also been proposed.

Another example of a homobifunctional conjugate which has found application in the prior art is the Bis-biotin conjugate used to examine the structure of avidin. Green, N. M., Konieczny, L., Toms, E. J., and Valentine, R. C., The Use of Bifunctional Biotinyl Compounds to Determine the Arrangement of Subunits in Avidin, *Biochemistry*, 125, 781–791 (1971). Where the two biotin moieties of the Bis-biotin conjugate were joined by a spacer moiety of approximately 18 Å, strong complexes or polymers were formed with the multivalent macromolecule avidin.

The second class of prior art small molecule bifunctional conjugates is the heterobifunctional conjugate. In contrast to the homobifunctional conjugate, the heterobifunctional conjugate employs a different chemical moiety at each end of the conjugate. Each of these chemical moieties is capable of interacting with a different specific binding partner. These prior art heterobifunctional conjugates have been used almost exclusively as modulators, wherein the binding of a specific binding partner to one of the chemical moieties hinders or precludes the simultaneous binding of the corresponding specific binding partner to the other chemical moiety. Simultaneous binding at both ends of the heterobifunctional conjugate is precluded by steric hindrance, generally caused by the use of shorter spacer lengths than those required to achieve the desired simultaneous binding where homobifunctional conjugates are employed as described above. In other words, the binding of a macromolecular specific binding partner to the modulator moiety of the conjugate sterically inhibits the binding of the specific binding partner to the chemical moiety responsible for producing signal.

The prior art heterobifunctional conjugates generally employ a small molecule ligand of interest, usually an analyte, as one of the chemical moieties of the conjugate. This chemical moiety can compete with free analyte, such as from a test sample, for a limited amount of specific binding partner for the analyte. The other chemical moiety of the heterobifunctional conjugate is usually a "surrogate" label such as an enzyme modulator or a prosthetic group or other cofactor for an enzyme. The surrogate label modulates the activity of the indicator label, usually an enzyme. These types of prior art heterobifunctional conjugates are generally of use in homogenous enzyme immunoassays, because the degree of activity of the enzyme is directly influenced by the antigen:antibody reaction. No separation step is required to determine the amount of enzyme activity attributable to the bound enzyme versus the activity attributable to the free enzyme, as in heterogenous enzyme immunoassays.

The enzyme modulated immunoassay is based on the ability of the small molecule ligand:enzyme modulator heterobifunctional conjugate to influence the activity of the indicator enzyme. See, for example, U.S. Pat. No. 4,134,792, which also discloses larger surrogate labeled conjugates. In this instance, the spacer moiety between the ligand moiety and the enzyme modulator moiety is relatively short, preferably being on the order of about 1–10 carbon atoms or heteroatoms in length; i.e., about 1.3 to about 14.0 Å.

The small molecule ligand:enzyme modulator heterobifunctional conjugate competes with ligand from a test sample for a limited amount of antibody. If the small molecule ligand:enzyme modulator heterobifunctional conjugate is bound to the antibody; i.e., through the ligand moiety of the conjugate, the enzyme modulator cannot affect the activity of the indicator enzyme. Modulators which increase or decrease the enzyme activity of the indicator enzyme can be used, although modulators which decrease enzyme activity; i.e., enzyme inhibitors, are more commonly used. In assays employing an inhibiting modulator, the observed enzyme activity will be inversely proportional to the concentration of analyte.

A similar type of homogenous enzyme immunoassay is based on the use of a small molecule ligand:enzyme cofactor heterobifunctional conjugate. In a broad sense, an enzyme cofactor operates as a positive enzyme modulator; i.e., a modulator which increases enzyme activity. Generally, enzymes may be divided into two groups: (1) enzymes where enzymatic activity is due solely to the protein nature of the enzyme; and, (2) enzymes where optimal enzymatic activity is dependent on a heat-stable, nonprotein structure called a cofactor. Immunoassays employing enzymes of this second group lend themselves to modulation through the use of a small molecule ligand:enzyme cofactor heterobifunctional conjugate.

Cofactors vary in nature from simple inorganic ions to more complex organic materials, many of which are derivatives of vitamins, such as biotin and flavin adenine dinucleotide (FAD). The organic cofactors are often referred to as coenzymes. In certain cases, as is typical with prosthetic groups, the cofactor is firmly bound, usually through a covalent linkage, to the protein moiety of the parent enzyme which is otherwise individually known as the apoenzyme. In the classical jargon of enzymology, the complete, enzymatically active enzyme:cofactor complex is termed a holoenzyme.

Residues of certain cofactors such as FAD, flavin mononucleotide (FMN), or heme, for example, provide particularly good enzyme prosthetic groups for use in a small molecule ligand:enzyme prosthetic group heterobifunctional conjugate. See, for example, U.S. Pat. No. 4,238,565, which also discloses larger surrogate labeled conjugates. In this case, the spacer moiety between the ligand moiety and the enzyme prosthetic group moiety is no more than 14 carbon atoms and 0–5 heteroatoms in length, and more commonly 1–6 carbon atoms and 1–3 heteroatoms in length; i.e., about 1.3 to about 14.0 Å.

According to U.S. Pat. No. 4,238,565, the ligand:prosthetic group heterobifunctional conjugate (for example, ligand:FAD) competes with the ligand in a test sample for a limited amount of antibody. If the ligand:FAD conjugate is bound by the antibody, it can no longer combine with the apoenzyme to form an enzymatically active holoenzyme. The observed enzyme activity is directly related to the concentration of analyte present in the test sample.

4. Heterogenous Purification and Detection Methods

One exception to the modulator type of use of the heterobifunctional conjugate is in the area of column chromatographic purification. A substance, such as a biologically active macromolecule, may be purified by passing a solution containing the substance through a chromatographic column in one of two ways. In one manner of purification, the column contains attached or immobilized groups or ligands that specifically bind to or otherwise pull specific impurities from the solution. In an alternate manner of purification, groups which specifically bind to the substance sought to be purified are immobilized on the column. These groups can pull the desired substance out of solution, through ligand-affinity reactions. In the latter case, the substance must later be eluted from the column.

General ligand affinity chromatography follows the latter approach and is based on the principle that a single immobilized ligand is able to adsorb, for example, a family of enzymes, such as dehydrogenases or kinases, with the isolated enzyme being subsequently eluted under conditions favoring biospecific elution. Often a cofactor or cofactor fragment is used as the general ligand.

Generally, a ligand can be immobilized by confining the ligand to a restricted region, such as a solid phase, through or over with the substance-containing solution is passed. There are numerous ways by which a ligand can be confined to a restricted space to establish a heterogenous purification system. A requisite is that immobilization of the ligand allow the substance-containing solution to easily pass through the restricted region to contact the ligand. Typically, this is accomplished by having the ligand and the substance in different phases.

A ligand can be immobilized by attachment to a solid or by entrapment in a liquid. Where the substance is a biological molecule, such as an antibody, it can be conveniently handled while in aqueous solution. The ligand can then be attached to a solid phase, such as an affinity gel. Alternately, the biological molecule can be in a gas phase or in a water-immiscible phase.

A ligand need not be physically attached to a phase in order for the ligand to be sufficiently immobilized to permit a heterogenous separation to take place. For example, the ligand can be immobilized by entrapment in a liquid phase. A ligand liquid phase can be separated from a liquid phase containing a substance of interest to be purified, such as a biologically active macromolecule, by a suitable semipermeable membrane.

Attachment of the ligand to a solid phase, such as for example an affinity gel, can be accomplished by a general interaction (for example, by non-specific, ion exchange bonding, or hydrophobic/hydrophilic interactions), specific interaction (for example, antigen-antibody, or biotin-avidin interaction), or by covalent bonding between the ligand and the solid phase. Alternately, an intermediate compound can be attached to the solid phase and the ligand can then be immobilized on the solid phase by attaching the ligand to the intermediate compound. Attachment of a ligand (called a free ligand) to the solid phase through an intermediate compound can facilitate the desired affinity purification. The intermediate compound which attaches the ligand to the solid phase, can itself be a ligand (a second ligand) with a specific binding affinity for the free ligand. Furthermore, the solid phase can be prepared or treated to have a particular affinity to the second ligand, thereby facilitating preparation of an affinity solid phase. Additional details regarding various heterogenous purification methods can be found in Rosevear, A., "Immobilized Biocatalysts" chapter 12 of *Molecular biology and Biotechnology*, edited by Walker, J. M., (1988), published by The Royal Society of Chemistry, and in Burton, S. J., "Affinity Chromatography" chapter , 3 of *Techniques in Molecular Biology*, volume 2, edited by Walker, J. M., (1987), published by Macmillan Pub. Co.

The insolubilized small molecule heterobifunctional conjugate AMP-ATP has been proposed for use in general ligand affinity chromatography. Lee, C. -Y., Larsson, P. O., and Mosbach, K., Synthesis of the Bifunctional Dinucleotide AMP-ATP and its Application in General Ligand Affinity Chromatography, *J. Solid Phase Biochem.*, 2 (1), 31–39 (1977). The ATP moiety (specific for kinases) is attached to a Sepharose® 4B (cross-linked agarose gel, Pharmacia, Uppsala, Sweden) column through a previously bound AMP moiety (specific for dehydrogenases). It has been reported that the ATP and AMP moieties retain their affinity behavior toward kinases and dehydrogenases, respectively, even when both are bound to the Sepharose column through the AMP moiety. An attempt to prepare a soluble AMP-ATP dinucleotide has proved unsuccessful. Id.

The prior art bifunctional conjugates used for affinity chromatography are generally difficult to make and have a short shelf life. Additionally, the prior art bifunctional conjugates tend to only poorly or loosely bind to various solid supports. Loose binding of the bifunctional conjugate to the solid support can permit significant amounts of the conjugates to be lost when one or more washing or elution steps of the solid support is carried out.

Furthermore, the particular small molecule heterobifunctional conjugate AMP-ATP, has the deficiency of being restricted to use for enzyme-cofactor affinity chromatography.

A frequent problem with ligand affinity chromatography occurs upon elution of a biologically active macromolecule, such as an antibody, from the affinity solid phase. Typically, the reagents used to dissociate the biological molecule from the solid phase immobilized ligand can cause some loss of biological activity to the eluted biological molecule. This can occur because the affinity constant between the ligand and the substance usually causes the ligand to tightly bind to the biological molecule, thereby enabling the ligand to pull the biological molecule out of solution. Hence, disruption of the affinity bond between the solid phase bound ligand and the biological molecule adhered to the ligand can cause the biological molecule to become damaged or denatured.

It would therefore be advantageous to have an immobilized or solid phase bound ligand which can bind to a biological molecule with a variable degree of an apparent affinity constant of the biologically active macromolecule for the ligand. A lower apparent affinity constant can allow the biological molecule to be bound less tightly to the ligand, thereby facilitating elution of an undamaged biological molecule from the immobilized ligand.

None of these prior art bifunctional conjugates has been applied to nephelometric or turbidimetric assay procedures. Moreover, only homobifunctional conjugates have even been suggested for use in the formation of large complexes, as is required in nephelometry or turbidimetry. The homobifunctional conjugate is useful only for linking up like molecules. It would be advantageous to have a soluble heterobifunctional conjugate capable of agglomerating dissimilar macromolecules. Such a heterobifunctional conjugate would be of particular use in NIIA's.

Additionally, it would also be advantageous to have a heterobifunctional conjugate capable of immobilization, as by strong binding to a solid support, and capable of use in a heterogenous purification and/or detection method for a macromolecule.

5. The Use of Avidin and Biotin in Immunoassays

Avidin and biotin are both naturally occurring compounds. Avidin is a relatively large macromolecular protein and is found in egg whites. Avidin contains four subunits. Biotin is a relatively small, stable, water-soluble vitamin. Each of the four subunits of an avidin molecule is capable of specifically binding to a molecule of biotin. The binding reaction between avidin and biotin is very strong, with the binding constant being approximately $10^{15}$ L/mole. The very strong nature of this bond has been found to persist even when biotin is conjugated, by means of its carboxyl group, to another molecule, or when avidin is attached to another molecule. When biotin is conjugated to another molecule, the resulting conjugate is usually referred to as a biotinylated compound; e.g., a biotinylated protein. A biotinylated protein may, for example, quickly become strongly bound to a corresponding avidin-attached molecule. This feature of linking up biotinylated compounds with avidin conjugates has been employed, with varying degrees of success, mostly in heterogenous immunoassays.

Two such applications pertain to sandwich immunoassays. In one instance, the avidin:biotin bond is utilized at the label end of the sandwich. This is seen in U.S. Pat. No. 4,228,237, wherein a biotinylated specific binding partner for the ligand to be measured is employed in conjunction with enzyme-labeled avidin. In another instance, the biotin:avidin bond may be used at the insolubilized end of the sandwich formed in a sandwich immunoassay. For example, U.S. Pat. No. 4,298,685 teaches the use of insolubilized avidin which is ordinarily added after the labeled sandwich has been formed in solution. Where the unlabeled antibody of the sandwich has previously been tagged with biotin, the insolubilized avidin is able to capture the labeled sandwich from the solution. These applications are not applicable to nephelometry or turbidimetry. Moreover, the additional conjugation steps required for preparing reagents makes such methods less attractive economically.

Avidin has also been used in homogenous immunoassays as the enzyme modulator label component of a larger surrogate labeled conjugate, which is used in a manner similar to the previously discussed small molecule ligand:enzyme modulator heterobifunctional conjugates. Avidin is the natural inhibitor of biotin-containing enzymes such as pyruvate carboxylase. When the biotin moiety of these enzymes is tied up, i.e., complexed with avidin, the activity of the enzyme ceases or is diminished. This is because biotin is a required cofactor of these enzymes, and, where the biotin moiety is incapable of functioning as a cofactor, enzyme activity is inhibited. Avidin may thus be used as a modulator label, due to its ability to modulate or control the activity of biotin-containing enzymes which, when allowed to act upon a substrate, yield a measurable signal in certain homogenous immunoassay systems.

U.S. Pat. No. 4,550,075 discloses avidin as the modulator label component of a larger labeled conjugate for use in a homogenous immunoassay. The labeled conjugate of U.S. Pat. No. 4,550,075 takes advantage of the large molecular size of avidin, which, at approximately 63,000 Daltons, is considerably larger than most modulator labels, i.e. enzyme inhibitors. This enables avidin to alleviate a steric hindrance problem typically encountered with larger surrogate labeled conjugates. For example, where a small molecule ligand:enzyme modulator heterobifunctional conjugate is used, the relative small size of the typical low molecular weight enzyme modulator is comparable to that of the ligand portion of the conjugate, and the modulator is therefore able to function effectively in the assay. Where, however, the ligand is much larger than the usual enzyme modulator, such as where the ligand is an antigen, the typical enzyme modulator is dwarfed by the size of the ligand, and the activity of the modulator label is sterically inhibited even in the absence of binding by the ligand component to its specific binding partner.

This steric hindrance problem has been addressed to some extent in the previously cited U.S. Pat. No. 4,238,565, wherein it is suggested that a slightly longer spacer moiety be employed where the ligand is a larger molecule of relatively high molecular weight. In any event, the spacer moiety may not exceed about 14 carbon atoms and 0–5 heteroatoms in length. The objective is that steric hindrance should occur only when the ligand moiety of the conjugate is bound to its specific binding partner, but not while the ligand moiety of the conjugate is free. U.S. Pat. No. 4,550,075, on the other hand, simply takes advantage of the inability of large ligands, such as antigens, to sterically hinder the activity of the macromolecular enzyme modulator avidin. Steric hindrance occurs only when the ligand moiety is bound to its specific binding partner.

The avidin:biotin bond has not been made of use in nephelometric or turbidimetric procedures, although the high specificity and strong nature of the bond would seemingly make it desirable in such procedures. The only use of avidin:biotin in complex formation is the previously noted use of Bis-biotin to agglomerate avidin. This procedure is not of use in nephelometry or turbidimetry. It would therefore be advantageous to apply the avidin:biotin bond to nephelometric and turbidimetric assay methods.

It would also be advantageous to apply the avidin:biotin bond to a heterogenous purification and/or detection method.

SUMMARY OF THE INVENTION

The present invention provides a novel bidentate conjugate which is applicable to a variety of immunochemical procedures for measuring an analyte of interest, particularly where the formation of large complexes is required or desired. The bidentate is of particular use in nephelometric and turbidimetric procedures and for a heterogenous purification method using immobilized bidentate. The bidentate conjugate of the present invention is essentially a soluble small molecule heterobifunctional conjugate which is capable of simultaneous binding and, ultimately, large complex formation. Specifically, the bidentate conjugate, or bidentate, is a soluble heterobifunctional conjugate having two different small molecule ligands, or bidentate members, each of which is capable of specifically binding to a different macromolecule. Where the formation of large complexes is desired, the macromolecules must be polyvalent. The bidentate members are attached through an adequate spacer moiety such that each bidentate member can simultaneously bind to its corresponding specific binding partner.

Where the bidentate is intended for use in a nephelometric or turbidimetric procedure, the first member of the bidentate is selected to be identical or analogous to the analyte of interest. The second bidentate member is the small molecule ligand portion of a ligand:specific binding partner pair. The ligand can, for example, be biotin where avidin is the specific binding partner. In the presence of the specific binding partner to the ligand (e.g., avidin where biotin is the ligand) and antibody to the analyte of interest, the bidentate will act as a link to form scattering complexes. Where avidin is the specific binding partner, each avidin molecule will preferably bind with two bidentates through the biotin member of each bidentate, while the remaining member of each bidentate will bind to antibody.

The present invention also provides a novel heterogenous purification method. The method has the steps of immobilizing a bidentate conjugate, contacting the immobilized bidentate conjugate with a liquid comprising a first macromolecular specific binding partner capable of adhering to the bidentate conjugate, and separating the immobilized bidentate conjugate with the adhered first macromolecular specific binding partner from contact with the liquid. The separation step results in obtaining a purified first macromolecular specific binding partner or a purified liquid. The spacer moiety of the bidentate conjugate can be at least about 22 Å in length. The second bidentate member can be biotin and the first bidentate member can be N-acetylprocainamide.

The bidentate conjugate can be immobilized by attaching the second bidentate member of the bidentate conjugate to a solid. The second macromolecular specific binding partner can be attached to the solid prior to the immobilizing of the bidentate. Thus, the bidentate conjugate can be immobilized on the solid by contacting the second bidentate member of the bidentate conjugate with the second macromolecular specific binding partner attached to the solid. In this manner, the second macromolecular specific binding partner can act as an intermediate compound.

The heterogenous purification method can comprise the additional step of removing the first macromolecular specific binding partner from contact with the first bidentate member of the bidentate conjugate in a manner such that the first macromolecular specific binding partner retains upon removal from contact with the bidentate conjugate a substantially undiminished biological activity as compared to the biological activity of the first macromolecular specific binding partner prior to its adherence to the bidentate conjugate.

Removal of the first macromolecular specific binding partner can results in regenerating the bidentate conjugate immobilized on the solid, thereby allowing the solid-supported conjugate to be used again as an affinity matrix.

Removal of the first macromolecular specific binding partner from contact with the first bidentate member of the bidentate conjugate can be carried out by a method selected from the group consisting of contacting the immobilized bidentate conjugate with an acidic medium, by mass-displacement, or by changing the pH, or the ionic strength or the temperature of an eluting buffer used to elute the first macromolecular specific binding partner.

The first macromolecular specific binding partner can be an antibody to the first bidentate member. Additionally, the first bidentate member can be identical or analogous to an analyte of interest. Furthermore, the analyte of interest can be selected from the group consisting of haptens, hormones, polypeptides, oligonucleotides, and vitamins. Preferably, the analyte of interest is a hapten with a molecular weight between about 100 and 1500 Daltons.

The hapten itself can be selected from the group consisting of theophylline, digoxin, disopyramide, lidocaine, N-acetylprocainamide, procainamide, propanolol, quinidine, amykamycin, chloramphenicol, gentamicin, kanamycin, netilmycin, tobramycin, tricyclic antidepressants, ethosuximide, phenobarbital, phenytoin, primidone, valproic acid, acetaminophen, acetylsalicylic acid, methotrexate, drugs of abuse (such as morphine, codeine, and heroin, and their metabolites), DNP, 1-substituted-4-hydroxy-2-nitrobenzene, and 4-substituted- 2-nitro-trialkylanilinium salts.

A more detailed embodiment of the heterogenous purification method can have the steps of: (a) selecting a bidentate conjugate comprising a first bidentate member attached to a second bidentate member through a spacer moiety, wherein the first and second bidentate members are different small molecule ligands, and each of the first and second bidentate members is capable of specifically binding to its respective and different first and second macromolecular specific binding partners; (b) attaching the second macromolecular specific binding partner to a solid phase; (c) immobilizing a bidentate conjugate on the solid phase by attaching the second bidentate member of the bidentate conjugate to the second macromolecular specific binding partner attached to the solid phase; (d) contacting the immobilized bidentate conjugate with a liquid comprising the first macromolecule specific binding partner, and; (e) separating the immobilized bidentate conjugate from contact with the liquid, thereby obtaining a purified first macromolecular specific binding partner or a purified liquid.

The present invention also includes within its scope, a process for the detection of a biological substance in a test sample. This process can have the steps of: (a) immobilizing the bidentate conjugate comprising a ligand on a solid phase; (b) contacting the ligand with a liquid phase biological substance having a specific binding affinity for the ligand, and; (c) detecting the biological substance.

The detecting step can be carried out by detecting the ligand-bound biological substance, by detecting any remaining liquid phase biological substance or by eluting the biological substance from the ligand prior to the detecting step and then detecting the eluted biological substance.

The solid phase can be a macromolecular insoluble material selected form the group consisting of agarose, polystyrene, polyacrylamide, nylon, cross-linked dextran, glass, plastic, and filter paper.

The present invention also includes within its scope an affinity chromatography method for the isolation of a specific antibody from a solution containing the antibody, comprising the steps of: (a) attaching the bidentate conjugate to a solid, wherein the bidentate conjugate comprises a ligand; (b) contacting the bidentate conjugate with a solution comprising an anti-ligand antibody, and; (c) separating the bidentate conjugate with the ligand bound antibody from contact with the solution.

Thus, the present heterogenous method can be used to purifying and/or to detect a biological molecule. The bidentate conjugate of the present invention is used in the heterogenous purification and/or detection method by immobilizing the bidentate conjugate on a solid phase. As set forth above, one of the macromolecular specific binding partners can be bound to the solid phase and treated with the bidentate conjugate. In this manner, one member of the bidentate will bind to its macromolecular binding partner attached to the solid phase, thereby immobilizing the bidentate on the solid phase. The solid phase thereby becomes an affinity matrix having the other bidentate member with its ligand available for selectively binding to its second and different macromolecular binding partner.

The length of the spacer moiety of the bidentate conjugate can be adjusted to permit a loose bonding of the free ligand of the bidentate to the biological molecule. Dissociation of the biological molecule from the ligand is then possible under mild conditions that allow the dissociated biological molecule to retain substantially all of its biological activity.

DETAILED DESCRIPTION OF THE INVENTION

Figure 1A:
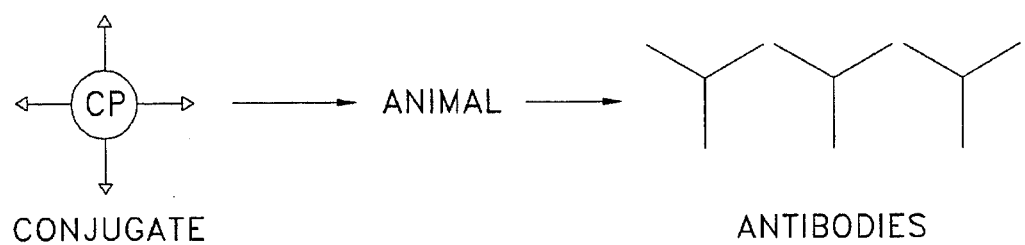
FIG. 1 depicts an inhibition immunoassay procedure using a specific embodiment of the bidentate conjugate of the present invention.

In the context of this disclosure, the following terms shall be defined as follows unless otherwise indicated:

Ligand: the smaller molecule in a complex or conjugate in which the smaller molecule specifically binds to a larger molecule or substance. The ligand may be naturally occurring or it may be artificially manipulated.

Specific binding partner: the larger molecule or substance in a complex or conjugate in which the specific binding partner specifically binds to a smaller molecule. The specific binding partner has a specific binding affinity for the ligand to the exclusion of other substances. The specific binding partner may be naturally occurring or artificially manipulated. Antibody fragments, for example, are included within this definition.

Ligand analog: an analog of the ligand molecule that can bind to the specific binding partner of the ligand in much the same manner as the ligand. The term "ligand" as used herein is generally intended to embrace ligand analogs, immunochemically equivalent materials, and any specific binding affinity substance whether natural or man-made.

Small molecule ligand: a ligand of less than about 7,000 Daltons in size. The small molecule ligand may be a piece or fragment of a larger ligand, such as an antigen. Where the small molecule ligand is an antigen fragment, the fragment must be recognized by antibody to the antigen with the same or similar degree of affinity that the antibody would have for the whole antigen.

Macromolecule: a larger molecule or substance of greater than about 10,000 Daltons in size.

Simultaneous binding: the ability of both bidentate members of the same bidentate to be bound to their specific binding partners at the same time. The binding of one specific binding partner may in fact occur prior in time to the binding of the other specific binding partner.

A novel bidentate conjugate is provided in accordance with the present invention. What is meant by the term bidentate conjugate is a soluble small molecule heterobifunctional conjugate having two chemical moieties, or bidentate members, which function as small molecule ligands and are attached through an adequate spacer moiety. The two small molecule ligands are each capable of specifically binding to a different macromolecule. Specific examples of small molecule ligands which may be used in the bidentate of the present invention include: hormones such as insulin, steroid hormones, and thyroid hormones; polypeptides; oligonucleotides; vitamins such as $B_{12}$, folic acid, and biotin; and haptens such as 1-substituted-2,4-dinitrobenzene (also known as dinitrophenol, or DNP) and drugs, including the bronchodilator theophylline and drugs of abuse such as morphine, codeine, cocaine, heroin, amphetamines and their metabolites and derivatives.

In the interest of clarity, the bidentate members will be referred to as a first bidentate member and a second bidentate member. The first and second bidentate members are ordinarily the ligand portion of a small molecule ligand:specific binding partner pair. Two preferred small molecule ligand:specific binding partner pairs are hapten:antibody and biotin:avidin. Other examples of small molecule ligand:specific binding partner pairs include: hormone:receptor; polypeptide: antibody; oligonucleotide:complementary DNA or RNA; vitamin $B_{12}$: intrinsic factor; folate:folate binding protein; and, insulin:anti-insulin.

It has surprisingly been found that such a soluble, small molecule heterobifunctional conjugate can be relatively easily synthesized and can be utilized to link together two dissimilar macromolecules. Further, where the macromolecular specific binding partners of the respective bidentate members are each polyvalent, the unusual formation of large complexes, formed through the small molecule heterobifunctional conjugate, has been observed. The soluble nature of the bidentate of the present invention greatly improves the reaction kinetics over a bound bifunctional conjugate.

Where the bidentate is intended for use in a nephelometric or turbidimetric assay method, the first bidentate member is selected to be identical or analogous to an analyte of interest, usually a hapten, which may be present in a test sample. What is necessary is that the first bidentate member be able to compete with free analyte for the same specific binding partner, usually an antibody. Preferably, the analyte is monovalent. The bidentate of the present invention is particularly useful in nephelometric or turbidimetric inhibition assays where the analyte of interest is a hapten, or analog thereof, with a molecular weight between about 100 and 1500 Daltons. The second bidentate member is the ligand portion of a small molecule ligand:specific binding partner pair. The specific binding partner must be polyvalent in order for large complexes to form. It is preferred that the specific binding partner be divalent. The latter group includes whole antibodies and $F(ab')_2$ fragments.

The synthesis of the bidentate of the present invention is relatively simple, once the first and second bidentate members are selected. Where the bidentate is intended for use in a nephelometric, turbidimetric, or other competitive type of assay procedure, the bidentate members will preferably be selected as suggested above. Where other uses are intended, the specific binding partners of the bidentate members will ordinarily be selected first. These are the substances which are preferably desired to be linked together. The first and second bidentate members will then be selected as the corresponding small molecule ligands which specifically bind to the larger specific binding partners previously chosen.

There are many methods known in the art for linking together the members of a bifunctional conjugate through a spacer moiety. See, for example, U.S. Pat. No. 4,134,792, U.S. Pat. No. 4,238,565, and Green, N. M., Konieczny, L., Toms, E. J., and Valentine, R. C., The Use of Bifunctional Biotinyl Compounds to Determine the Arrangement of Subunits in Avidin, *Biochem. J.*, 125, 781–791 (1971). These methods generally involve typical condensation, addition, and substitution reactions between chemical moieties which may or may not have been activated prior to such reactions.

Several conjugation methods are set forth in the Examples which follow. It is generally convenient if the selected method includes the insertion of a compound which is one in a series of homologs in a particular class of compounds. For example, the alkane diamine ($NH_2$—$(CH_2)N$—$NH_2$) class of compounds contains ethanediamine (N=2), propanediamine (N=3), butanediamine (N=4), pentanediamine (N=5), and so forth. Where the synthesis process includes the insertion of one of these homologs, other homologs may be easily substituted to vary the chain length of the spacer connecting the two members of the bidentate.

The particular chemical composition of the spacer moiety will depend, to some extent, on the nature of the chemical sites available on the respective bidentate members for connecting the spacer moiety. Typical heteroatoms, including nitrogen, oxygen, sulfur, and phosphorus, may be used in the spacer moiety in addition to carbon atoms. Generally the spacer moiety will be aliphatic, although aromatic groups may be involved. In the typical divalent chain, where single bonds employing carbon nitrogen, or oxygen are incorporated into the spacer moiety, each such atom can be expected to increase the spacer moiety length by about 1.2 to about 1.5 Å.

The precise method used to link the bidentate members together, through the spacer moiety, is not critical. What is important is that both bidentate members retain their ability to effectively bind with their specific binding partners following synthesis of the bidentate. This consideration may affect the exact chemical site chosen for connection to the spacer moiety. Ordinarily it is desired to maximize the exposure of the active site or sites of the particular bidentate member which allows for the specific binding reaction to occur.

The length of the spacer moiety connecting the bidentate members has been found to be of particular importance in regulating the ability of both bidentate members to simultaneously bind to their respective specific binding partners. For example, if the spacer moiety between the bidentate members is relatively short, steric hindrance will inhibit, and can even prevent, the desired simultaneous binding. Steric hindrance occurs where a bifunctional conjugate employs a relatively short spacer length, and the specific binding partners of the members of the bifunctional conjugate are very large. For example, as previously noted, avidin has a molecular weight of approximately 63,000 Daltons, while the typical antibody has a molecular weight of about 150,000 Daltons. If one of these macromolecules is bound to a bifunctional conjugate with a short spacer moiety, the other molecule may be unable to simultaneously bind to the same bifunctional conjugate, as is the case with prior art modulated assays employing heterobifunctional conjugates. Where large complex formation is desired, this may also be inhibited.

The minimum spacer length required to enable the simultaneous binding of two homobifunctional conjugate members to their respective specific binding partners may be determined by any of a number of methods known in the art. See, for example, Larsson, P. O., and Mosbach, K., Affinity Precipitation of Enzymes, *Elsevier/North-Holland Biomedical Press*, 98 (2), 333–338 (1979), and Green, N. M., Konieczny, L., Toms, E. J., and Valentine, R. C., The Use of Bifunctional Biotinyl Compounds to Determine the Arrangement of Subunits in Avidin, *Biochem. J.*, 125, 781–791 (1971). Similar methods may be used to determine the minimum spacer length required for the simultaneous binding of two bidentate members. Where the bidentate of the present invention is intended for use in a competitive assay, wherein signal is produced pursuant to simultaneous binding by the bidentate, the minimum spacer length required to achieve simultaneous binding may be determined under the identical assay conditions ultimately desired but in the absence of free competitive analyte. Under these conditions, the spacer moiety length is increased until measurable signal is first observed. This is the minimum spacer length. The important consideration is that the chosen method provide an opportunity to detect binding efficacy.

One convenient method for determining minimum spacer length is through the use of standard nephelometric or turbidimetric procedures. These methods are useful where the bidentate can be used to form large complexes; i.e., complexes large enough to form scattering centers, even where this is not the ultimate intended use of a particular bidentate. This method is applicable only where polyvalent specific binding partners are available for both bidentate members. Specifically, bidentates which vary only with respect to spacer length (otherwise known as homologs) are brought into contact with their respective multivalent specific binding partners. Complex formation will begin to be observed at the minimum spacer moiety length which allows simultaneous binding. Optimal minimum spacer length will ordinarily be a little longer than minimum spacer length. The amount of complex formation will, however, generally reach a plateau within several carbon atoms or heteroatoms of the minimum spacer length.

Where the bidentate of the present invention is intended for use in a NIIA, the sensitivity of the NIIA can also suffer if the spacer moiety between the bidentate members is too long. This occurs, for example, where the second bidentate member binds to a macromolecule, such as avidin, having more than two binding sites for the second bidentate member. In such an instance, the longer spacer length may allow for more than two bidentates to bind to each macromolecule.

Using avidin as an example, there are four available biotin binding sites on the avidin molecule. These binding sites occur in pairs, with both binding sites of a pair existing in relatively close proximity on a face of the molecule. Where the spacer length of the bidentate conjugate is in the proper range, the bidentate will, due to steric hindrance, be able to bind to only one binding site of the pair existing on the same face of the avidin molecule. However, the longer the spacer length of the bidentate, the further the antibody (bound to one end of the bidentate) will be from the avidin molecule (bound to the other end of the bidentate). Ultimately, a point is reached where the spacer length is sufficiently long to enable the binding of a second bidentate to an avidin binding site adjacent to a paired site to which a first bidentate has previously bound.

It is preferred to use only one binding site of each pair of binding sites on the avidin molecule, i.e., two total bonds per avidin molecule, in order to form linear aggregates of sufficient length to fold into scattering complexes. In this way, one free analyte molecule can effect a break in the growth of the linear aggregate by essentially displacing the first bidentate member which would otherwise bind with its polyvalent specific binding partner, usually an antibody, to ultimately form scattering complexes. Where both binding sites of a pair are occupied on a face of the avidin molecule, it will take two free analyte molecules to effect the same break in the growth of the linear aggregate.

In the optimal range, the spacer length of the bidentate for use in a NIIA will be long enough to allow the simultaneous binding of the respective binding partners to both the first and second bidentate members, but short enough to inhibit binding of the bidentate to more than two binding sites on a single specific binding partner.

The bidentate of the present invention is superior to prior art developer antigens used in NIIA's. The bidentate is a purified organic chemical which can last for years at room temperature. It is also simple to make, purify, and characterize, and quality control expenses are minimal as compared to prior art developer antigens. The bidentate also eliminates the prior art problem of nonproductive binding, because each bidentate has only one hapten moiety. Thus, only one arm of an antibody can bind to a particular bidentate.

A NIIA using the bidentate of the present invention is similar to prior art NIIA's only with respect to the preliminary step of antibody production. In either case, antibodies to the analyte of interest are first generated by injecting into an animal a carrier protein conjugated to a plurality of analyte molecules, as is shown in FIG. 1A where the analyte of interest is a hapten.

Figure 1B:
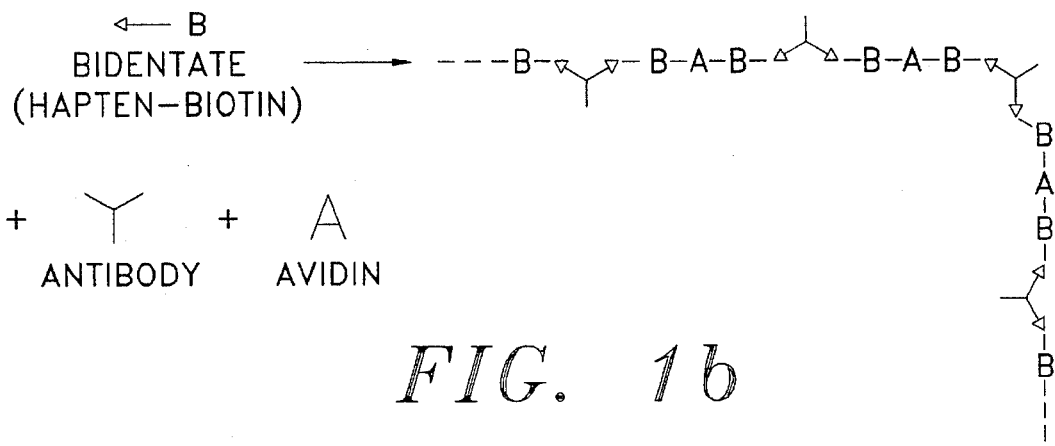

The antibody which has thus been raised against the analyte of interest is brought into contact with the analyte-:ligand bidentate of the present invention, along with specific binding partner to the ligand, and test sample. The interaction among these reagents may take place in any suitable reaction vessel. Where little or no free analyte is present in the test sample, the bidentate conjugate reacts with available antibody and specific binding partner to the second bidentate member to form scattering complexes. This reaction is shown in FIG. 1B where a hapten is the analyte of interest as well as the first bidentate member, antibody is the specific binding partner to the first bidentate member, biotin is the ligand, or second bidentate member, and avidin is the specific binding partner to the second bidentate member.

Figure 1C:
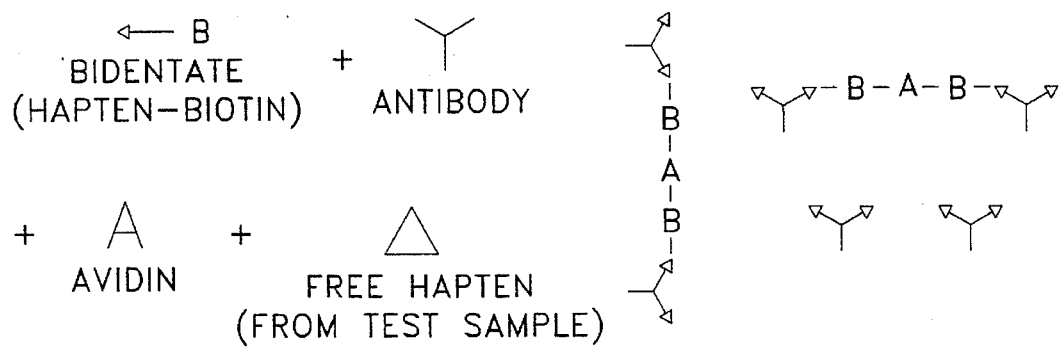

In the presence of free analyte, however, the amount of complexing will be inhibited by the binding of free analyte to the available antibody, as shown in FIG. 1C. This occurs because free analyte, unlike the analyte:ligand bidentate conjugate, cannot bind with specific binding partner to the ligand in order to link together with antibody to form scattering complexes. The amount of signal, measured as an indication of the degree of scattering complex formation, is inversely proportional to the amount of free analyte present in a test sample.

In the interest of clarity, a detailed discussion is provided only with regard to the synthesis and use of several theophylline-biotin bidentates. It will, of course, be recognized that similar synthesis methods and NIIA procedures for haptens other than theophylline will work equally as well following the same general procedures. Examples of drugs which can be assayed effectively in a NIIA using the bidentate of the present invention include therapeutic drugs such as digoxin, disopyramide, lidocaine, procainamide, propanolol, quinidine, amykamycin, chloramphenicol, gentamicin, kanamycin, netilmycin, tobramycin, tricyclic antidepressants, ethosuximide, phenobarbital, phenytoin, primidone, valproic acid, acetaminophen, acetylsalicylic acid, methotrexate, and drugs of abuse such as morphine, codeine, cocaine, heroin, amphetamines and their metabolites and derivatives. Examples of other haptens which can be assayed using the bidentate conjugate include DNP, 1-substituted-4-hydroxy-2-nitrobenzene, 4-substituted-2-nitrotrialkylanilinium salts and fluorescein. The analyte of interest is preferably employed as one of the bidentate members, with the other bidentate member being a different small molecule ligand, such as biotin.

In order to demonstrate the effect of the length of the spacer moiety, homologs (identical in every respect but spacer length) of two different theophylline-biotin bidentate conjugates were synthesized and evaluated under nephelometric conditions. In the interest of clarity, the two bidentate conjugates are referred to herein as bidentate conjugate I and bidentate conjugate II. Bidentate conjugate II differs from bidentate conjugate I in having a carbon atom adjacent to the theophylline moiety rather than the nitrogen atom located adjacent to the theophylline moiety in bidentate conjugate I. The synthesis of both conjugates involves the insertion of a diamine between the theophylline moiety (first bidentate member) and the biotin moiety (second bidentate member) of the bidentate. The chain length of the spacer moiety of the bidentate may be varied through the selection of a particular diamine for the synthesis process. In this case, spacer length is measured from the biologically active alicyclic ring structure of biotin, with the 5-carbon aliphatic tail being incorporated into the spacer. A similar synthetic process may be used to produce other bidentates, including other hapten-biotin bidentates.

Initially, primary amine derivatives of theophylline may be prepared from commercially available starting theophylline derivatives as a first step in the synthesis process. Other processes may be used to prepare primary amine derivatives of other haptens. Where bidentate conjugate I is prepared, an excess of a diamine is refluxed with the starting derivative 8-bromotheophylline. This generally takes place under a nitrogen atmosphere for a period of two to seventy-two hours, depending upon the particular diamine selected, and results in product I.

Where bidentate conjugate II is prepared, it is necessary to use carbonyldiimidazole (CDI) and N-hyroxysuccinimide (NHS) to activate the carboxylic group of the starting derivative theophylline-8-butyric acid before the selected diamine can be inserted. Activation is carried out by dissolving theophylline-8-butyric acid in anhydrous dimethylformamide (DMF), followed by heating to about 70° C. with the subsequent addition of an equimolar quantity of CDI. The reaction temperature must be maintained at about 70° C., usually for approximately 15 minutes, before it is cooled back to room temperature. An equimolar quantity of NHS is subsequently added to the cooled reaction mixture and stirred overnight at room temperature. An excess of diamine may then be added to the activated reaction mixture. This results in product II.

The completion of the reaction producing the required primary amine derivative may be determined by a thin layer chromatographic (TLC) analysis of either reaction mixture I or reaction mixture II, using glass TLC plates coated with silica gel and an ultraviolet indicator.

The reaction mixtures must then be evaporated to a small volume under vacuum, with the concentrated reaction mixtures being purified by standard silica gel column chromatography using a gradient chloroform:methanol mixture. The eluted fractions containing the pure primary amine derivatives of theophylline are pooled and evaporated to dryness in a rotary evaporator. The white-yellowish crystalline solids obtained upon evaporation may be used for the next reaction without further purification. Theophylline monoamine derivatives have a molar absorptivity of about $1.9 \times 10^3$ at 295 nm in methanol.

Figure 2:
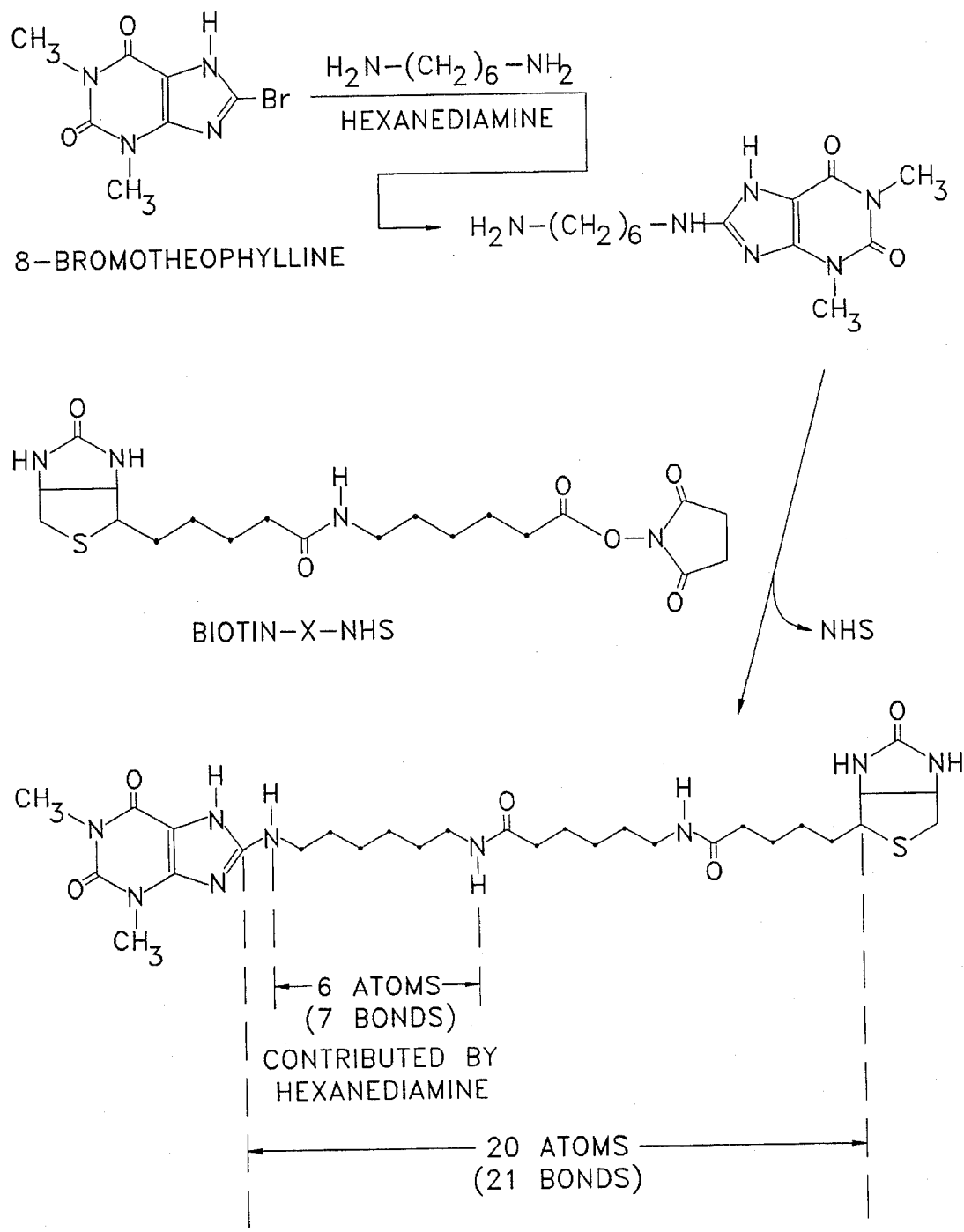
FIG. 2 schematically represents the synthesis of a bidentate conjugate I homolog.
Figure 3:
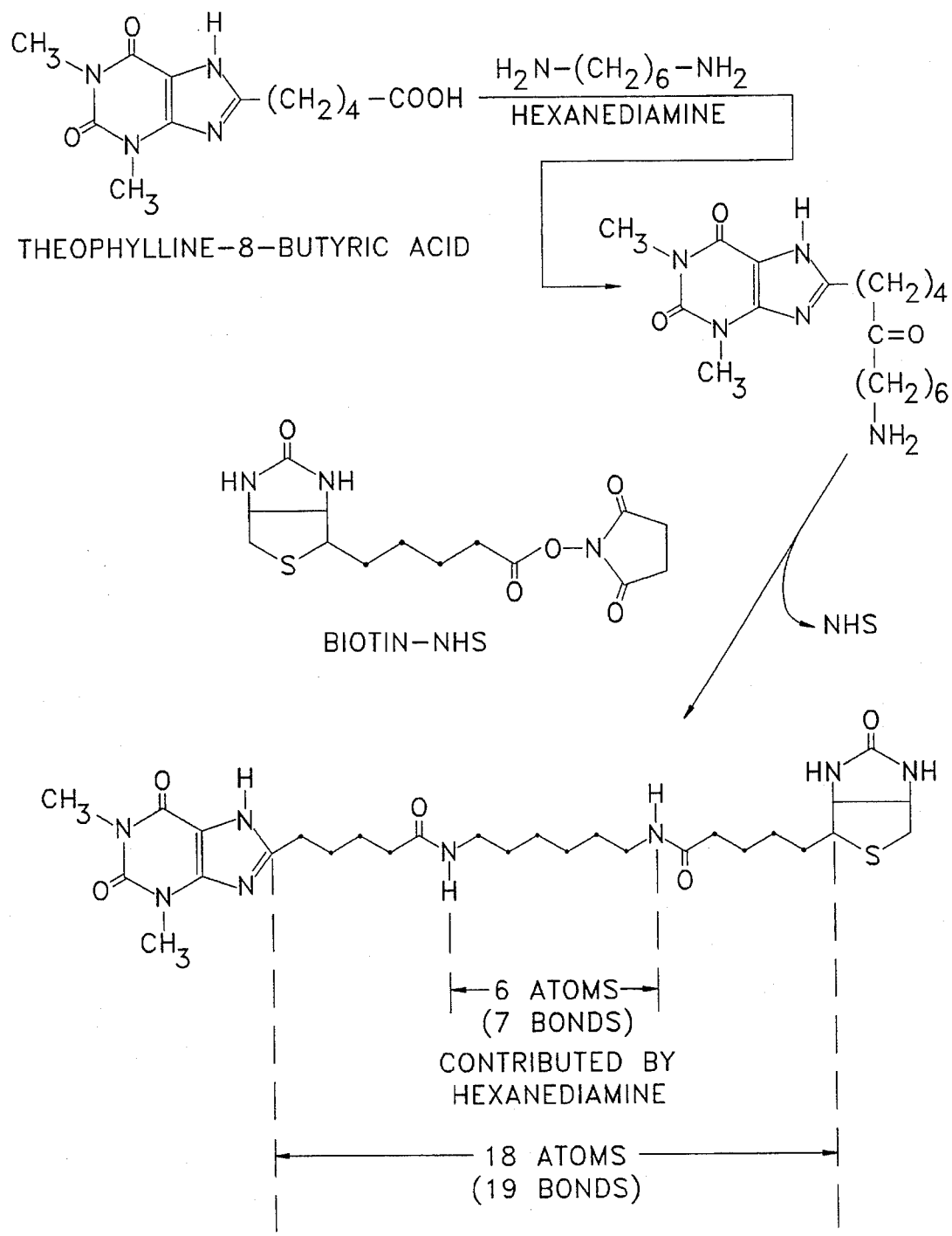
FIG. 3 schematically represents the synthesis of a bidentate conjugate II homolog.

Biotin-theophylline conjugate I is prepared by dissolving the crystalline solids containing the primary amine derivatives of theophylline from reaction mixture I in anhydrous DMF and then mixing in the activated N-hyroxysuccinimide ester of caproamidobiotin (biotin-X-NHS), as is schematically shown in FIG. 2. Primary amine derivatives of other haptens may similarly be condensed with biotin-X-NHS, or any other chemical moiety containing an available activated carboxyl group. This solution is also stirred overnight at room temperature. Biotin-theophylline conjugate II is similarly prepared, with the exception that the crystalline solids containing the primary amine derivatives of theophylline from reaction mixture II are mixed with the N-hydroxysuccinimide ester of biotin (biotin-NHS), as is shown in FIG. 3. In either case, the desired products usually separate out of DMF as white, flocculent solids. The product may be collected on a filter paper and purified to a single spot in a TLC test either by preparative thin layer chromatography or by column chromatography.

The bidentate conjugate homologs may be used in nephelometry or under other assay conditions to determine optimal spacer length. The optimal minimum spacer length does not vary significantly with different proportions of bidentate, avidin, and biotin. Moreover, the same minimum spacer length data will generally apply where haptens other than theophylline are used as one of the members of a hapten-biotin bidentate conjugate, although some slight variation may be observed, due to the greater variation in the size and shape of the specific binding partners for these ligands as compared to avidin. Where small molecule ligands other than biotin are incorporated as one of the bidentate members, a somewhat greater degree of variation can be expected. Nevertheless, a study of the theophylline-biotin bidentate provides sufficient minimum spacer length data to provide the starting basis for the synthesis of any number of bidentates.

A bidentate conjugate according to the present invention can also be used in a heterogenous purification or biological molecule detection method. Thus, an affinity matrix can be prepared by attaching a carrier molecule, such as avidin, modified avidin or streptavidin to a suitable solid, such as one of the numerous commercially available affinity gels used for affinity chromatographic purposes. The avidin-attached solid can then be treated with a biotin-containing bidentate. The solid-avidin-biotin bidentate thereby becomes an affinity matrix. The free bidentate member can then act as an affinity ligand for its macromolecular specific binding partner.

Thus, the affinity matrix can be prepared by first treating a suitable solid with a macromolecular specific binding partner for one of the ligands of the bidentate conjugate. This step can be followed by immobilizing the bidentate conjugate to the treated solid by contacting the treated solid with the bidentate conjugate. By immobilization of the bidentate conjugate it is meant that the bidentate conjugate becomes securely attached to the solid phase. Thus, upon contact of the solid phase attached bidentate conjugate with a liquid phase, the bidentate conjugate does not detach in significant amount from the solid phase. The liquid phase can contain a biological molecule having a specific binding affinity for a ligand of the bidentate conjugate.

The prepared affinity matrix can be used to remove a macromolecule from solution by contacting the affinity matrix with a solution contain a macromolecular specific binding partner for the free ligand of the immobilized bidentate conjugate. In this manner there can be obtained either a purified macromolecule or a solution purified by binding the macromolecule to the bidentate. If desired, the macromolecule drawn out of the solution can be easily eluted from the affinity matrix. Elution can be carried out by washing the macromolecule saturated affinity matrix with an acidic liquid.

Alternately, the affinity matrix and purification steps can be carried out simultaneously as follows. The solid phase is first treated with the macromolecular specific binding partner for one of the ligands of the bidentate conjugate as above. Immobilization of the bidentate conjugate to the solid and adherence of the macromolecule in the solution to be purified can then be carried out together by treating the affinity solid at the same time with both the bidentate and the macromolecule-containing solution.

The spacer moiety between the two ligands of the bidentate conjugate is of a sufficient length that simultaneous binding of one ligand of the bidentate to the macromolecule bound to the solid and of the other ligand of the bidentate to the macromolecule in the solution can occur. A spacer length of about 22 Å can be suitable for this purpose.

The present invention can advantageously be used to perform a controllable affinity chromatography. The free ligand of the immobilized bidentate can be selected to be an antigen to a particular antibody of interest. Hence, when a solution containing the antibody is passed over the bidentate affinity matrix, the antibody can be removed from the solution. An antibody can be eluted from an affinity matrix by using a chaotropic eluant, or by using a low pH (i.e. between about pH 2 and about pH 5) buffer. These eluants can disrupt the antibody-ligand bonding, dissociating the antibody from the ligand, thereby allowing the antibody to be eluted to a harvesting container.

Typically, during the treatment with a chaotrope or low pH buffer, some labile antibody will lose biological activity, possibly be becoming denatured to a varying degree. We have found that by varying the spacer length between the two ligands of the bidentate, the apparent binding tenacity or apparent affinity constant between the free ligand member of an immobilized bidentate and a macromolecular specific binding partner for the free ligand, such as an antibody can be altered. This modification or fine-tuning of the apparent affinity constant is possible because the spacer moiety length can be increased or decreased in increments of about 1.2 Å.

The intrinsic affinity constant of the antibody towards the ligand is not changed by varying spacer length. A change in the apparent affinity constant is due to altering the amount of steric hindrance between the affinity matrix immobilized bidentate and the incoming antibody molecule. In this manner, it is possible to alter the strength of the apparent affinity binding between a macromolecule, such as an antibody, and the free ligand of the immobilized bidentate. Generally for a given macromolecule, the shorter the spacer moiety of the bidentate, the looser the binding of the macromolecule to the free ligand of the immobilized bidentate conjugate.

By altering the length of the spacer moiety so that a macromolecule is only loosely or marginally adhered to the free ligand member of the bidentate, the macromolecule can be eluted from contact with the bidentate using a less stringent eluant or by a shorter contact time with an eluant. A less stringent eluant can cause less denaturing of the captured macromolecule. Elution of the captured macromolecule can be carried out by, for example, (1) changing the pH, or (2) the ionic strength of an eluting buffer, (3) mass-action displacement (i.e. by using a solution of a hapten to a captured antibody, to displace the antibody from the immobilized ligand), and (4) changing the temperature of the eluting buffer. Typically an elution buffer temperature change of ±5° C. can suffice to permit elution of a captured macromolecule. Generally, the present method can be carried out permitting the binding of the macromolecule to the immobilized, free ligand member at a first lower temperature (of the liquid phase containing the macromolecule), followed by elution of the captured macromolecule at a second higher temperature (of the eluting buffer). By these elution methods, a macromolecule such as an antibody can be harvested with minimal denaturation.

The present method can be used to purify a solution of a wide variety of macromolecules such as a solution of polyclonal antibodies. Polyclonal antibody is raised from an animal and harvested from its sera. Such a solution of a polyclonal antibody usually contains many antibody molecules with various specificities and affinity constants, and also non-specific immunoglobulins admixed. It can be desirable to eliminate or harvest a certain fraction of the antibody molecules of particular specificity and/or affinity constant from the polyclonal antibody solution.

A heterogenous purification method within the scope of the present invention can also be used to detect and quantify the amount of a substance or an analyte of interest in a test sample, such as in a sample of a physiological fluid. An analyte-containing fluid solution can be passed over the immobilized bidentate conjugate. A label attached to either the analyte or to the bidentate conjugate can then be detected to detect the bound analyte. Alternately, known methodologies can be used to detect the reduced level of analyte in the solution that was contacted with the immobilized bidentate or the bound analyte can be eluted from the solid phase and then detected by various means, including by photometric immunoassay techniques, such as nephelometry and turbidimetry.

EXAMPLE 1

Synthesis of Bidentate Conjugate I

The synthesis of bidentate conjugate I using hexanediamine (N=6) as the variable for insertion into the spacer is schematically shown in FIG. 2. The N=6 homolog of bidentate conjugate I was produced in the following manner:

An excess of hexanediamine ($NH_2$—$(CH_2)_6$—$NH_2$) was refluxed with 8-bromotheophylline under a nitrogen atmosphere for a period of 24 hours. The end of the reflux reaction was determined by TLC analysis of the reaction mixture, using glass TLC plates coated with silica gel and an ultraviolet indicator.

The reaction mixture was then evaporated to a small volume under vacuum. The concentrated reaction mixture was mixed with a small quantity of silica gel and dried on a hot plate with the silica gel-sample mixture then being carefully loaded onto the top of a silica gel column using chloroform as the starting eluant. The column was eluted with solvent containing varying amounts of methanol in chloroform. When the gradient composition reached 20% methanol in chloroform, the column was eluted with a mixture containing 20% methanol, 4% ammonia, and 76% chloroform. The fractions containing the pure N-(8-theophylline)-6-aminohexylamine were pooled and evaporated to dryness in a rotary evaporator. White-yellowish crystalline solids were used for the next reaction without further purification.

Equimolar quantities of the N-(8-theophylline)-6-aminohexylamine crystalline solids were dissolved in anhydrous DMF, then mixed with the corresponding molar quantity of biotin-X-NHS and left stirring at room temperature for 24 hours. The desired products separated out of DMF as white, flocculent solids, and were collected on filter paper and purified to a single spot in a TLC test by column chromatography.

The chain length of the spacer moiety is controlled by the diamine ($NH_2$—$(CH_2)_N$—$NH_2$) selected for use in the synthesis of the bidentate. For example, where hexanediamine is selected for the first synthesis step, six carbon atoms are contributed to the spacer moiety chain length, as shown in FIG. 2. In this instance, the approximate length of the spacer moiety is 26.0 Å. The chain length obtained from the insertion of various diamines into the spacer of bidentate conjugate I, using a procedure similar to that used to prepare the N=6 homolog, is shown in Table I.

TABLE I

Length of Spacer Moiety in Bidentate Conjugate I Homologs

| Diamine | Total Number of Atoms in Spacer | Approximate Spacer Length (Å) |
|---|---|---|
| N = 2 | 16 | 21.0 |
| N = 3 | 17 | 22.2 |
| N = 4 | 18 | 23.5 |
| N = 5 | 19 | 24.8 |
| N = 6 | 20 | 26.0 |
| N = 7 | 21 | 27.3 |
| N = 8 | 22 | 28.5 |

EXAMPLE 2

Evaluation of Effect of Spacer Moiety on Efficacy of Bidentate Conjugate

Once the series of bidentate conjugates identified in Table 1 were prepared, the conjugates were evaluated under nephelometric conditions to determine the effect of spacer length on the amount of signal generated by a particular bidentate conjugate.

A. Minimum Spacer Length

Minimum spacer length was determined by detecting the amount (rate) of signal generated by each of the conjugates identified in Table 1 in the presence of anti-theophylline antibody and avidin. This is the same reaction as is shown in FIG. 1B. No free theophylline was added to inhibit complexing as would be the case in a NIIA as shown in FIG. 1C. The purpose of these measurements was simply to determine minimum spacer length for optimal binding at stoichiometric proportions of bidentate, antibody, and avidin.

The reagents were prepared as follows: monoclonal antibody against theophylline was diluted 1:13:3 in ICS™ Diluent (Beckman Instruments, ICS™ Reagent). Avidin, purchased from Boehringer Mannheim, was dissolved in ICS diluent at a concentration of 0.13 mg/mL. Various dilutions of each of the bidentate conjugates listed in Table 1 were dissolved in 0.1M phosphate buffer, pH 5.5.

Nephelometric measurements were taken on an ICS™ nephelometer (Beckman Instruments) by placing 600)L of ICS Buffer (Beckman Instruments, ICS™ Reagent) into an ICS™ vial (Beckman Instruments), and injecting 42)L of antibody solution and 42)L of avidin solution. After the injection transient subsided and the baseline was obtained, 42)L of the bidentate conjugate were added and the instrument triggered to record the peak rate signal.

Figure 4:
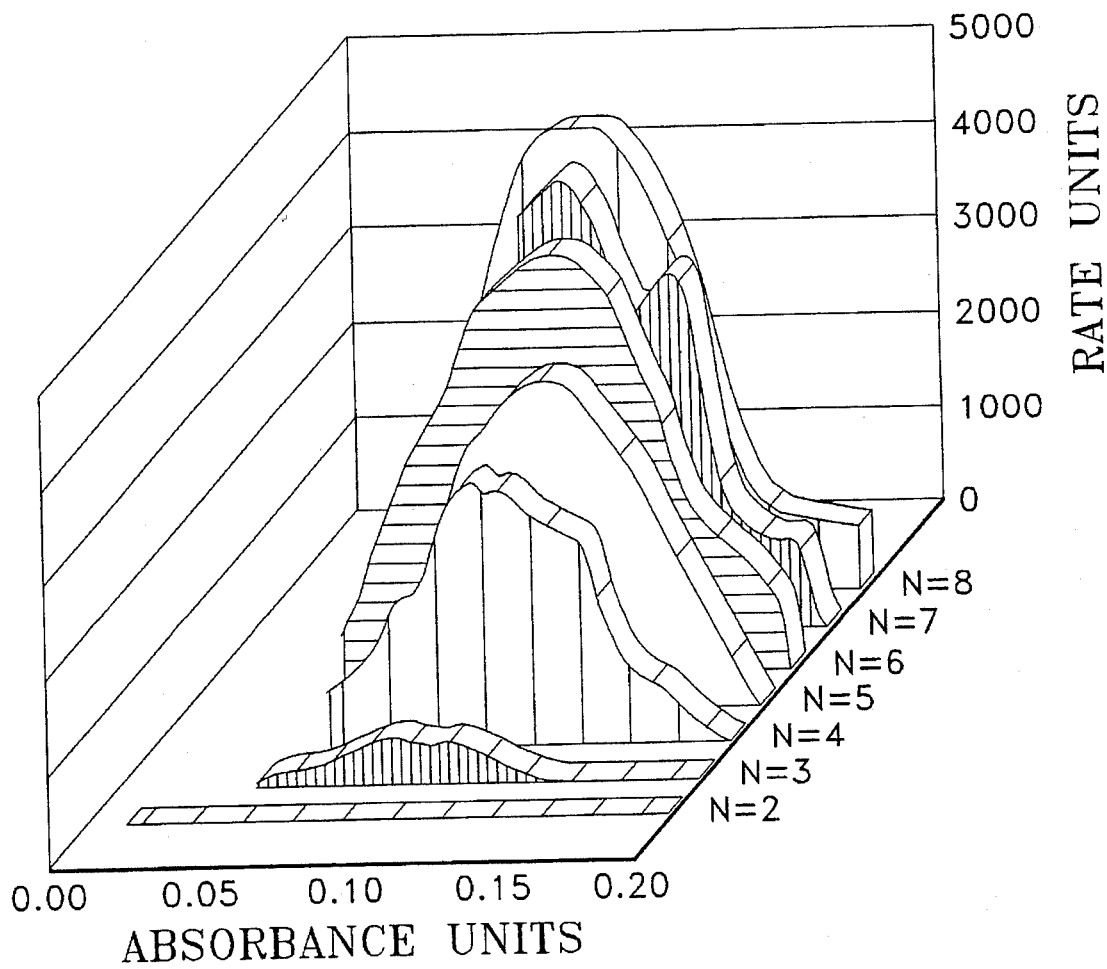
FIG. 4 demonstrates the effect of spacer length on the ability of both members of the bidentate conjugate to simultaneously bind to their specific binding partners.

The results for N=2 through N=8 are reported in FIG. 4. In FIG. 4, the units on the horizontal axis represent bidentate concentration based on absorbance at 295 nm. The units on the vertical axis are ICS™ rate units, obtained using the ICS™ Manual Mode Card M33 (Beckman Instruments).. For high rate signals, above 2000 units, the ICS™ lower gain card was used and the results calculated for M33 gain.

As is seen in FIG. 4, the lowest homolog of bidentate conjugate I (N=2), having 17 bonds (16 atoms) between the theophylline ring carbon and the alicyclic ring carbon of biotin failed to yield measurable complex formation. The next higher homolog (bidentate conjugate I, N=3) began to show measurable complexing. The higher homologs (N=4 through N=8) produced correspondingly higher signal until a plateau was reached at N=8. This study shows that a minimum spacer length of approximately 22.2 Å is required in order to produce signal where theophylline is employed as the first bidentate member and biotin is employed as the second bidentate member. Optimally, the spacer length should be at least about 23.5/(bidentate conjugate I, N=4).

B. Maximum Spacer Length

Maximum spacer length was determined by detecting the amount (rate) of signal generated by the homologs of bidentate conjugate I, listed in Table 1 as N=4 through N=8, under the inhibition conditions typically encountered in an NIIA.

The assay procedure was carried out similarly to that set forth in Part A of Example 2, except that the concentrations of the bidentate conjugates were kept constant, rather than varying the concentrations of each bidentate conjugate, as was done in Part A to determine minimum spacer length. Each bidentate conjugate was dissolved in 0.1M phosphate buffer, pH 7.5, and further diluted in such a manner that its absorbance at 295 nm was 0.136. The 0.136 absorbance value was selected from Part A of Example 2 as being at or near the point at which maximum rate signal, was observed; i.e., the bidentate concentration at which maximum complex formation occurred. Varying, rather than fixed, amounts of free theophylline were added in order to effect the inhibition schematically shown in FIG. 1C.

Figure 5:
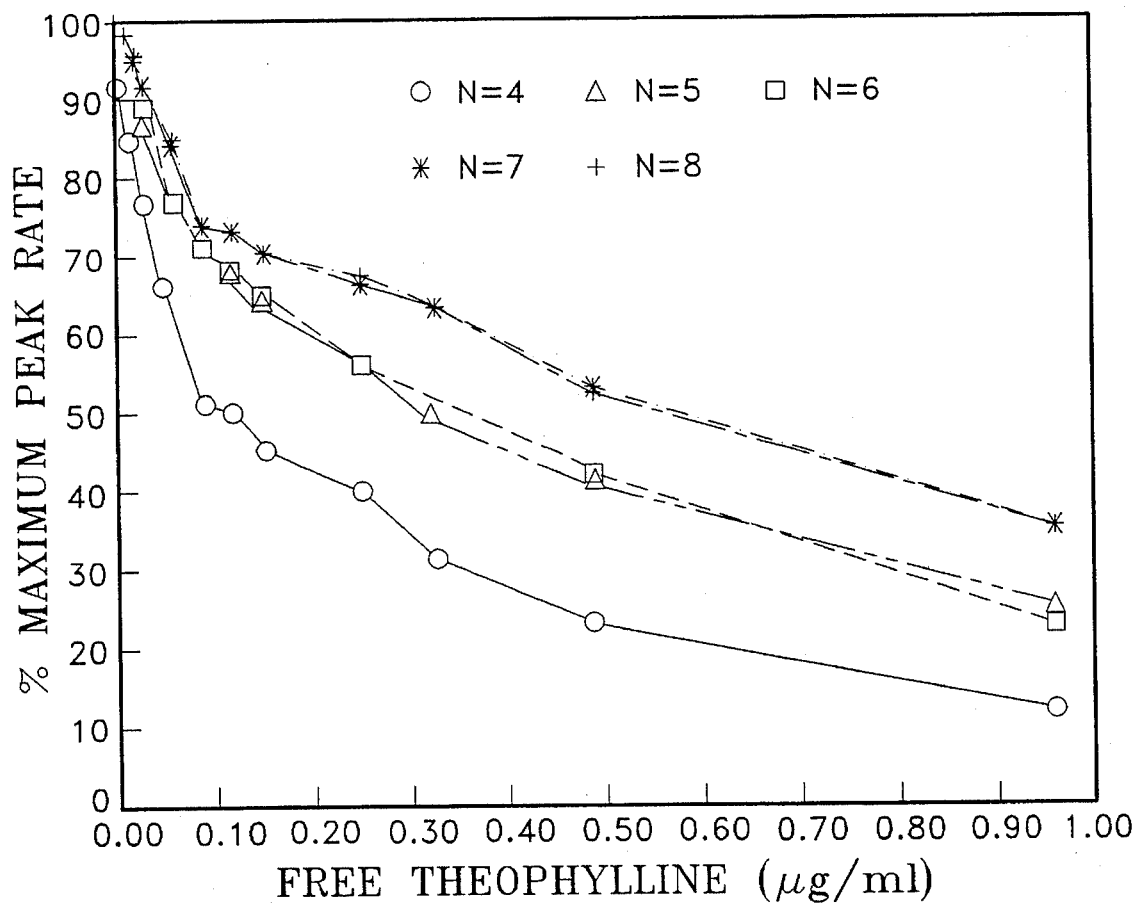
FIG. 5 demonstrates the effect of spacer length on the sensitivity of a NIIA using a specific embodiment of the bidentate conjugate of the present invention.

The results of this assay are displayed in FIG. 5. Each point on the graph shown in FIG. 5 represents the peak rate obtained for a particular bidentate conjugate homolog in the presence of anti-theophylline antibody, avidin, and a given amount of theophylline. The highest peak rate is obtained in the absence of analyte, in other words, at 0.00)g/mL of theophylline. The peak rate obtained in the absence of analyte is the maximum peak rate attainable under the parameters of the assay, and is expressed as 100% of peak rate signal. In the presence of free analyte, the peak rate will be inhibited. The degree of inhibition increases, and the peak rate signal decreases, with increasing amounts of free hapten or analyte.

The greatest sensitivity of the theophylline NIIA was obtained using the N=4 homolog of bidentate conjugate I. Sensitivity represents the degree of change in peak rate signal effected by a given concentration of free analyte. A concentration of 0.10)g/mL of free theophylline, was able to effect an approximate 50% drop in the maximum peak rate signal when the N=4 homolog was used. Where the N=5 or N=6 homologs were used, a 50% drop in maximum peak rate signal was not observed until an approximate concentration of 0.30)g/mL of free theophylline was added to the system. The N=7 and N=8 homologs exhibited a sensitivity comparable to that of prior art NIIA's using traditional developer antigens, i.e., approximately 0.50)g/mL of theophylline was required to be added to the system before a 50% decrease in signal was measured. All of the N=4 through N=8 homologs of bidentate conjugate I were found to operate satisfactorily in a NIIA under the assay conditions studied in this experiment, although the N=4 homolog was found to be superior for purposes of sensitivity and demonstrated a marked improvement over the sensitivity of prior art NIIA's. The N=5 and N=6 homologs also gave superior results. It is expected that there will be some slight variation in the optimal maximum spacer length observed for a particular assay where different proportions of bidentate, antibody, and avidin are used, as well as where other assay conditions are varied.

EXAMPLE 3

Bidentate Conjugate I in NIIA for Theophylline

A typical NIIA for theophylline was run using the N=6 homolog of bidentate conjugate I. The assay was run under conditions similar to those set forth in Part B of Example 2.

The reagents were prepared as follows: monoclonal antibody against theophylline was diluted 1:13.3 in ICS™ Diluent (Beckman Instruments, ICS™ Reagent). Avidin, purchased from Boehringer Mannheim, was dissolved in ICS diluent at a concentration of 0.13 mg/mL. The bidentate conjugate was dissolved in 0.1M phosphate buffer, pH 5.5, and further diluted in such a manner that its optical density at 295 nm was 0.136. ICS™ Drug Calibrator (Beckman Instruments, ICS™ Reagent), containing 10)g/mL theophylline, was diluted in ICS™ Diluent at ratios of 1:10, 1:20, 1:30, 1:40, 1:60, 1:80, 1:100, 1:200, 1:400, 1:600, and 1:1000.

Nephelometric measurements were taken on an ICS™ nephelometer (Beckman Instruments) by placing 600)L of ICS Buffer (Beckman Instruments, ICS™ Reagent) into an ICS™ vial (Beckman Instruments), and injecting 42)L of Drug Calibrator or blank sample, 42)L of antibody solution, and 42)L of avidin solution. An instrument gain setting of Manual Mode M33 was used. After the injection transient subsided and the baseline was obtained, 42)L of the bidentate conjugate was added and the instrument triggered to record the peak rate signal. The results are set forth in Table II.

TABLE II

| DRUG CALIBRATOR | | Rate Units | Percent |
|---|---|---|---|
| Dilution | Concentration μg/ml) | (Average of 3 Measurements) | of maximum Peak Rate |
| 1:10 | 0.966 | 666 | 25 |
| 1:20 | 0.483 | 1123 | 42.4 |
| 1:30 | 0.322 | 1353 | 51.1 |
| 1:40 | 0.242 | 1485 | 56.1 |
| 1:60 | 0.161 | 1710 | 64.6 |
| 1:80 | 0.120 | 1787 | 67.5 |
| 1:100 | 0.096 | 1890 | 71.4 |
| 1:200 | 0.048 | 2057 | 77.7 |
| 1:400 | 0.024 | 2290 | 86.5 |
| 1:600 | 0.016 | 2407 | 90.9 |
| 1:1000 | 0.0096 | 2453 | 92.7 |
| Blank | — | 2647 | 100.0 |

EXAMPLE 4

Synthesis of Bidentate Conjugate II

A second bidentate conjugate was formed to confirm the results obtained for bidentate conjugate I and to demonstrate an alternate synthesis method. The synthesis of bidentate conjugate II using hexanediamine as the variable for insertion into the spacer is schematically shown in FIG. 3. The N=6 homolog of bidentate conjugate II was produced in the following manner:

Theophylline-8-butyric acid was dissolved in anhydrous DMF, then heated to about 70° C. with the subsequent addition of an equimolar quantity of CDI. The reaction temperature was maintained at about 70° C. for approximately 15 minutes, then allowed to cool to room temperature. An equimolar quantity of NHS was then added to the cooled reaction mixture and left stirring at room temperature overnight. An approximate three to six molar excess of hexanediamine ($H_2N—(CH_2)_6—NH_2$) was then added to the reaction mixture. The completion of reaction was determined by TLC analysis of the reaction mixture, using TLC plates coated with silica gel and an ultraviolet indicator.

The reaction mixture was then evaporated to a small volume under vacuum. The concentrated reaction mixture was mixed with a small quantity of silica gel and dried on a hot plate with the silica gel-sample mixture then being carefully loaded onto the top of a silica gel column using chloroform as the starting eluant. The column was eluted with solvent containing varying amounts of methanol in chloroform. When the gradient composition reached 20% methanol in chloroform, the column was eluted with a mixture containing 20% methanol, 4% ammonia, and 76% chloroform. The fractions containing the pure 6-(8'-theophylline butyric carboxamido)-hexylamine were pooled and evaporated to dryness in a rotary evaporator. White-yellowish crystalline solids were used for the next reaction without further purification.

An Equimolar quantity of the 6-(8'-theophylline-butyric-carboxamido)-hexylamine was dissolved in anhydrous DMF, then mixed with the corresponding molar quantity of biotin-NHS and left stirring at room temperature for 24 hours. The desired products separated out of DMF as white, flocculent solids, and were collected on a filter paper and purified to a single spot in a TLC test by preparative thin layer chromatography.

The N=5 homolog of bidentate conjugate II was prepared using an identical procedure with the exception that pentanediamine was used in place of hexanediamine. The spacer lengths for these two homologs are set forth in Table III.

TABLE III

Length of Spacer Moiety in Bidentate Conjugate II Homologs

| Diamine | Total Number of Atoms in Space | Approximate Spacer Length (Å) |
|---|---|---|
| N = 5 | 16 | 21.0 |
| N = 6 | 18 | 22.2 |

The N=2 homolog of bidentate conjugate I is equivalent to the N=5 homolog of bidentate conjugate II (21.0 Å). The N=3 and N=6 homologs of bidentate conjugates I and II, respectively, are also equivalent (22.2 Å). The N=5 homolog of the second series, like the N=2 homolog of the first series failed to yield measurable complexing. Comparable signals were obtained, however for the N=6 homolog of bidentate conjugate II and the N=3 homolog of bidentate conjugate I. This confirms that at least a 22.2 Å spacer moiety is required to achieve simultaneous binding of both bidentate members to their specific binding partners where theophylline and biotin are chosen as the first and second bidentate members, respectively.

EXAMPLE 5

Heterogenous Purification of a Polyclonal Anti-Procainamide Solution

A heterogenous purification method was carried out to reduce the population of anti-N-acetylprocainamide antibody molecules (anti-NAPA) from a solution of polyclonal antibody raised specific to procainamide (PA) in goat serum.

1. Preparation of a NAPA Affinity Column

A bidentate conjugate wherein one of the bidentate members was biotin and the other bidentate member was N-acetylprocainamide (NAPA) was prepared using the bidentate synthesis methodology previously set forth. As aliquot of 5.0 mL of Affigel-10 (BioRad Laboratories) was washed with deionized water and 0.1 M sodium phosphate buffer at pH 7.4. The Affigel was placed in a 50.0 mL capacity centrifugation tube and adjusted to a total volume of 10.1 mL with the same phosphate buffer. Avidin (165 mg dissolved in deionized water) was then added to the Affigel. The mixture was left in a cold room at 4° C. overnight. The Affigel gel was then washed eight times with 50 mL of the phosphate buffer to eliminate any excess avidin or N-hydroxysuccinimide. The total volume of the Affigel suspension was then adjusted to 6.0 mL using the phosphate buffer. A small amount of 4-hydroxyazobenzoic acid (HABA) was then added to the above gel, which then turned a pinkish color, indicating attachment of avidin to the gel matrix. The biotinylated NAPA bidentate conjugate dissolved in dimethylformamide was then added to the avidin-affinity gel (the solid phase) until the pinkish color became distinctively yellow, indicating that all the avidin's biotin binding sites were occupied by the biotinylated NAPA bidentate conjugate.

The solid phase affinity matrix was then washed with phosphate buffer until it became colorless, and packed into a column chromatography column. In this manner, an affinity column in which the immobilized affinity ligand was N-acetylprocainamide was prepared.

2. Purification of A Polyclonal Procainamide Antibody Solution

A. Goat polyclonal procainamide antiserum (40 mL) was obtained by harvesting blood samples from goats treated with a procainamide antigen using established and well known procedures for raising mammalian polyclonal antibody. This polyclonal antibody solution clearly contained a significant of one or more cross-reactants to procainamide as shown by the date obtained and set forth in Table IV below. This data was obtained by conducting a nephelometric inhibition immunoassay (NIIA) for procainamide using an Array™ Nephelometer (Beckman). The same amount of procainamide (PA) (µg/mL) was assayed using 0, 50 and 150 µg/mL of NAPA and an appropriate aliquot volume of the goat polyclonal procainamine antiserum.

TABLE IV

| PA (µg/mL) | NAPA (µg/mL) | Apparent Concentrations of PA (average of 3 assays)(µg/mL) |
|---|---|---|
| 3 | 0 | 2.84 |
| 3 | 50 | 4.87 |
| 3 | 150 | 5.61 |

The goat polyclonal procainamide antiserum was then treated with ammonium sulfate solution, as a pre-purification step, and the antibody enriched pellet obtained was dissolved in deionized water and dialyzed in the phosphate buffer to obtain 74 mL of a polyclonal procainamide antibody solution.

An aliquot of 35.0 mL of the polyclonal antibody solution was passed through the prepared N-acetylprocainamide bidentate conjugate affinity column. Fractions which absorbed at 280 nm were collected and pooled to a total of 30 mL. Aliquots of the 30 ml eluent were assayed by NIIA for procainamide using then ICS II Nephelometer (Beckman). The assayed aliquots had a nephelometric rate reading "out of range high" (ORH) at a 1:3 dilution; 2500 rate units at a 1:4 dilution, and; a 1760 rate units readout at a 1:4.5 dilution. Thus, it was determined that the 30 mL of eluent was primarily pure procainamide antibody, the cross-reacting NAPA antibody having been removed by the heterogenous purification method using the immobilized bidentate conjugate.

Cross-Reactivity of the Affinity Purified Procainamide Antibody

It was determined that the cross reactivity of the 30 mL of eluent (obtained by passing the procainamide polyclonal antiserum solution through the NAPA bidentate affinity column) towards NAPA was substantially reduced by the present method, thereby further indicating that this eluent contained essentially pure procainamide antibody, and the efficacy of the present method. Thus, a standard solution containing, 3 µg/mL of procainamide (PA) was mixed with various concentrations (0, 50 and 150 µg/mL) of NAPA and assayed by NIIA as previously set forth. The apparent PA concentrations obtained were recorded and are shown by Table V below.

TABLE V

| PA (µg/mL) | NAPA (µg/mL) | Apparent Concentrations of PA (µg/mL) |
|---|---|---|
| 3 | 0 | 2.74 |
| 3 | 50 | 3.47 |
| 3 | 150 | 3.87 |

Capacity of the NAPA-Affinity Column

B. The remaining 39 mL (of the 74 mL) of the ammonium sulfate antibody (IgG) solution, was passed through the affinity column. The fractions having 280 nm absorption were pooled to obtain about 39 mL and tested for activity using the ICS II Nephelometer. At a 1:3 dilution, it gave an ORH nephelometric rate signal. The same ORH for a 1:4 dilution was obtained. At 1:5 dilution, the rate was 3110 rate units and 1260 rate units for a 1:7.5 dilution. In order to determine the extent of depletion of NAPA in the 39 mL of eluent, the cross reactivity of this eluent solution was measured. The cross reactivity was higher than that shown in Table V, but lower (i.e. improved over) than that shown in Table IV.

3. Elution of NAPA Antibody from the Affinity Column

It was determined that the bonding between the solid-bound avidin and the biotin moiety of the biotinylated NAPA can withstand exposure to low pH solution. Thus, 0.01N hydrochloric acid was used, as set forth below, as an eluent to disrupt the bonding between the NAPA antibody and the NAPA ligand of the avidin-solid phase immobilized biotinylated NAPA bidentate conjugate.

The affinity column saturated with NAPA antibody from the polyclonal antibody solution, was washed with deionized water, and then with 5 mL of 0.01N hydrochloric acid, followed by additional deionized water. Fractions were collected until the absorption at 280 nm became baseline. The selected fractions were pooled to obtain approximately 20 mL. The pool was then dialyzed in phosphate buffer. The protein in the dialysis bag was identified to be goat immunoglobulin at about 1 mg/mL as determined by a standard nephelometric quantification using rabbit anti-goat antiserum. This eluted antibody was determined to be NAPA antibody by being reacted with an avidin conjugated biotinylated NAPA bidentate conjugate.

Immunoreactivity of the Affinity Purified NAPA Antibody

The eluted antibody retained immunoreactivity towards NAPA. The NAPA antibody obtained in section 3 above was titred with the matching avidin-biotin-NAPA bidentate conjugate using 3 different NAPA standards. The following dose-response relationship was obtained;

TABLE VI

| NAPA STDS. (µg/mL) | RATE UNITS | % B/Bo |
|---|---|---|
| 0 | 1350 | 100 |
| 2 | 1110 | 82.2 |
| 30 | 332 | 24.6 |

4. Regeneration of the NAPA-Affinity Column

The acid treated affinity column, as described in section 3 above, was washed with deionized water followed by washing with the phosphate buffer solution. Thus prepared affinity column was tested for its activity as described in the following section 5.

5. Affinity Chromatography Using the Regenerated Column

Using the affinity column as prepared in section 4, 39 ml of the partially purified procainamide antibody solution (obtained from the experiment described in section 2.B. above) was passed through, collecting fractions having a 280 nm absorption. The recovered and pooled fractions gave about 48 mL. This purified PA antibody solution not only had intact immunoreactivity but also gave improved and desired cross reactivity test results comparable to those shown in Table V above. This experiment established that the NAPA-affinity column is reusable.

The present invention has numerous advantages including the following:

1. A "universal" solid phase for a heterogenous purification method can be prepared by immobilizing a bidentate conjugate to a solid. The solid phase can then be used as an affinity matrix for macromolecule that can bind for the free ligand of the immobilized bidentate conjugate.

2. The affinity matrix can be easily prepared by, for example, contacting an avidin bound solid with a biotin bidentate conjugate.

3. A controllable affinity chromatography method can be carried out by varying the length of the spacer moiety of an immobilized bidentate conjugate.

Other types of bidentate conjugates using other bidentate members and different atoms or sequences of atoms in the spacer moiety are contemplated as being within the scope of this invention and will be apparent to those skilled in the art. The bidentate of the present invention is useful in any assay or procedure where the simultaneous binding of both bidentate members is required or desired. Optimal spacer moiety length can easily be determined using nephelometry or turbidimetric procedures where multivalent specific binding partners are available.

As this invention may be embodied in several forms, without departing from the essential spirit thereof, the invention is intended to be defined by the appended claims as opposed to the foregoing description.

We claim:

1. A heterogenous purification method with a solid phase and a liquid phase, the method comprising the sequential steps of:

(a) providing a bidentate conjugate comprising a first bidentate member attached to a second bidentate member through a spacer moiety wherein the spacer moiety comprises between about 16 atoms and about 22 atoms and the spacer moiety has a length between about 21 Å and about 29 Å, said first and second bidentate members being different small molecule ligands, each of the ligands being capable of specifically binding to their respective and different first and second macromolecular specific binding partners;

(b) immobilizing said bidentate conjugate on a solid phase;

(c) contacting the immobilized bidentate conjugate with a liquid phase comprising a first macromolecular specific binding partner capable of adhering in a specific binding affinity reaction to the bidentate conjugate;

(d) separating the immobilized bidentate conjugate with the adhered first macromolecular specific binding partner from contact with the liquid phase;

(e) eluting from said bidentate conjugate a first macromolecular specific binding partner with a substantially undiminished biological activity as compared to the biological activity of the first macromolecular specific binding partner prior to adherence to the bidentate conjugate, thereby obtaining a purified first macromolecular binding partner; and (f) regenerating the solid phase to thereby render it reusable for the purification of additional first macromolecular binding partner.

2. The method of claim 1, wherein the bidentate conjugate is immobilized by attaching the second bidentate member of the bidentate conjugate to the solid phase.

3. The method of claim 2, further comprising the step of attaching the second macromolecular specific binding partner to the solid prior to the immobilizing step.

4. The method of claim 3, wherein the bidentate conjugate is immobilized on the solid by contacting the second bidentate member of the bidentate conjugate with the second macromolecular specific binding partner attached to the solid.

5. The method of claim 1, wherein the eluting step is carried out by a method selected from the group consisting of contacting the immobilized bidentate conjugate with an acidic medium, by mass-displacement, and by changing the pH, or the ionic strength or the temperature of an eluting buffer used to elute the first macromolecular specific binding partner.

6. The method of claim 1, wherein the first macromolecular specific binding partner is an antibody to the first bidentate member.

7. The method of claim 1, wherein the first bidentate member has affinity binding characteristics which are identical or analogous to an analyte of interest.

8. The method of claim 7 wherein the analyte of interest is selected from the group consisting of haptens, hormones, polypeptides, oligonucleotides, and vitamins.

9. The method of claim 8 wherein the analyte of interest is a hapten with a molecular weight between about 100 and 1500 Daltons.

10. The method of claim 9 wherein the hapten is selected from the group consisting of theophylline; digoxin; disopyramide; lidocaine; N-acetylprocainamide; procainamide; propanolol; quinidine; amykamycin; chloramphenicol; gentamicin; kanamycin; netilmycin; tobramycin; tricyclic antidepressants; ethosuximide; phenobarbital; phenytoin; primidone; valproic acid; acetaminophen; acetylsalicylic acid; methotrexate; morphine; codeine; and heroin; dinitrophenol; 1-substituted-4-hydroxy-2-nitrobenzene; and 4-substituted-2-nitro-trialkylanilinium.

11. The method of claim 1 wherein the second bidentate member is biotin.

12. The method of claim 1 wherein the first bidentate member is N-acetylprocainamide.

13. The method of claim 1 wherein the spacer moiety is at least about 22 Å in length.

14. The method of claim 1 wherein both the first and second macromolecular specific binding partners are multivalent.

15. A heterogenous purification method, comprising the sequential steps of:

(a) selecting a bidentate conjugate comprising a first bidentate member attached to a second bidentate member through a spacer moiety, wherein the first and second bidentate members are different small molecule ligands and the spacer moiety comprises between about 16 atoms and about 22 atoms and the spacer moiety has a length between about 21 Å and about 29 Å, and each of the first and second bidentate members is capable of specifically binding to its respective and different first and second macromolecular specific binding partners;

(b) attaching the second macromolecular specific binding partner to a solid phase;

(c) immobilizing a bidentate conjugate on the solid phase by attaching the second bidentate member of the bidentate conjugate to the second macromolecular specific binding partner attached to the solid phase;

(d) contacting the immobilized bidentate conjugate with a liquid comprising the first macromolecule specific binding partner; and, (e) separating the immobilized bidentate conjugate from contact with the liquid, thereby obtaining a purified first macromolecular specific binding partner.

16. An affinity chromatography method for the isolation of a specific antibody for a ligand from a solution containing the antibody, comprising the steps of:

(a) attaching a bidentate conjugate to a solid, wherein the bidentate conjugate comprises a ligand and a spacer moiety, the spacer moiety comprising between about 16 atoms and about 22 atoms and the spacer moiety has a length between about 21 Å and about 29 Å;

(b) contacting the bidentate conjugate with a solution comprising a specific antibody for the ligand;

(c) separating the bidentate conjugate with the ligand bound antibody from contact with the solution; and (e) regenerating the solid to thereby render it reusable for the isolation of additional specific antibody.

17. The method of claim 16, further comprising the step of removing the antibody from contact with the ligand of the bidentate conjugate.

* * * * *